US012053617B2

(12) United States Patent
Melander et al.

(10) Patent No.: US 12,053,617 B2
(45) Date of Patent: Aug. 6, 2024

(54) DRUG DELIVERY DEVICE HAVING DAMPING MECHANISM

(71) Applicant: AMGEN INC., Thousand Oaks, CA (US)

(72) Inventors: Matias Melander, Copenhagen (DK); Jakob Halkjaer Pedersen, Virum (DK); Christian Plambech, Soeborg (DK); Adam B. McCullough, Westlake Village, CA (US); Julian Jazayeri, Woodland Hills, CA (US)

(73) Assignee: AMGEN INC., Thousand Oaks, CA (US)

( * ) Notice: Subject to any disclaimer, the term of this patent is extended or adjusted under 35 U.S.C. 154(b) by 691 days.

(21) Appl. No.: 16/601,824

(22) Filed: Oct. 15, 2019

(65) Prior Publication Data

US 2020/0114082 A1 Apr. 16, 2020

Related U.S. Application Data

(60) Provisional application No. 62/745,813, filed on Oct. 15, 2018.

(51) Int. Cl.
*A61M 5/178* (2006.01)
*A61M 5/24* (2006.01)
(Continued)

(52) U.S. Cl.
CPC ............ *A61M 5/24* (2013.01); *A61M 5/3129* (2013.01); *A61M 5/3148* (2013.01);
(Continued)

(58) Field of Classification Search
CPC ............ A61M 5/2033; A61M 5/31585; A61M 5/3157; A61M 5/24; A61M 5/3129;
(Continued)

(56) References Cited

U.S. PATENT DOCUMENTS

| 6,270,479 B1 * | 8/2001 | Bergens | A61M 5/2033 |
| | | | 604/156 |
| 7,901,377 B1 * | 3/2011 | Harrison | A61M 5/2033 |
| | | | 604/157 |

(Continued)

FOREIGN PATENT DOCUMENTS

| AU | 2014224340 B2 | 12/2016 |
| AU | 2014229581 B2 | 12/2016 |

(Continued)

OTHER PUBLICATIONS

International Application No. PCT/US2019/056174, International Search Report and Written Opinion, dated Feb. 2, 2020.

(Continued)

*Primary Examiner* — Nathan R Price
*Assistant Examiner* — Tania Ismail

(57) ABSTRACT

A drug delivery device includes a housing defining a shell having a proximal and a distal end, a needle assembly at least partially disposed within the housing at the proximal end, a drive assembly at least partially disposed within the housing, and a damper mechanism at least partially disposed within the housing adjacent to the distal end. The housing further defines a longitudinal axis extending between the proximal end and the distal end. The needle assembly includes a syringe barrel containing a medicament and a needle or a cannula. The drive assembly is operably coupled to the needle assembly to urge the medicament through the needle or cannula. The damper mechanism is operably coupled to the drive assembly and the housing. Upon activating the drive assembly, the damper mechanism dampens an effect thereof.

23 Claims, 13 Drawing Sheets

(51) Int. Cl.
  *A61M 5/31* (2006.01)
  *A61M 5/20* (2006.01)
  *A61M 5/315* (2006.01)
  *A61M 5/32* (2006.01)
(52) U.S. Cl.
  CPC ..... *A61M 5/2033* (2013.01); *A61M 2005/208* (2013.01); *A61M 2005/2086* (2013.01); *A61M 2005/3143* (2013.01); *A61M 5/31585* (2013.01); *A61M 2005/3267* (2013.01)
(58) Field of Classification Search
  CPC .......... A61M 5/3148; A61M 2005/208; A61M 2005/2086; A61M 2005/3267; A61M 2005/3143
  See application file for complete search history.

(56) References Cited

U.S. PATENT DOCUMENTS

| | | | | |
|---|---|---|---|---|
| 8,579,866 | B2* | 11/2013 | Morgan | A61M 5/3137 604/187 |
| 9,474,859 | B2* | 10/2016 | Ekman | A61M 5/2033 |
| 2001/0005781 | A1 | 6/2001 | Bergens et al. | |
| 2010/0094217 | A1 | 4/2010 | Wyrick | |
| 2011/0077595 | A1 | 3/2011 | Eich et al. | |
| 2017/0361025 | A1 | 12/2017 | Cowe | |
| 2018/0161507 | A1 | 6/2018 | Fabien et al. | |
| 2018/0221584 | A1* | 8/2018 | Grimoldby | A61M 5/31505 |

FOREIGN PATENT DOCUMENTS

| | | |
|---|---|---|
| CL | 201502524 | 2/2016 |
| CL | 201502525 | 2/2016 |
| CN | 103998076 A | 8/2014 |
| TW | 200940118 A | 10/2009 |
| TW | 201720474 A | 6/2017 |
| TW | 201740989 A | 12/2017 |
| WO | WO-95/31235 A1 | 11/1995 |
| WO | 2008072715 A1 | 6/2008 |
| WO | 2012007246 A1 | 1/2012 |
| WO | WO-2012/025639 A1 | 3/2012 |
| WO | 2016205962 A | 12/2016 |
| WO | WO-2016/205962 A1 | 12/2016 |
| WO | WO-2018/226565 A1 | 12/2018 |
| WO | WO-2020/037256 A1 | 2/2020 |

OTHER PUBLICATIONS

Eurasian Patent Application No. 202191037, Office Action, dated Oct. 28, 2021.
Chile Patent Application No. 202100891, Office Action and Search Report, dated May 10, 2022.
Chinese Patent Application No. 2019800644141, First Office Action, mailed Jul. 28, 2022.
Chinese Patent Application No. 2019800644141, Second Office Action, mailed Feb. 27, 2023.
India Patent Application No. 202117021154, First Examination Report, mailed Feb. 12, 2022.
Argentinian Patent Application No. P190102925, First Office Action, mailed Jun. 14, 2023.
Notice of Allowance received in counterpart Chinese Application No. 2019800644141, dated Jul. 11, 2023.
Office Action received in counterpart Japanese Application No. 2021-520125, dated Aug. 22, 2023.
Office Action received in counterpart Taiwanese Patent Application No. 108137051, dated Aug. 18, 2023.
Office Action received in counterpart Japanese Patent Application No. 2021-520125, dated Mar. 5, 2024.
Examination Report received in counterpart Australian Patent Application No. 2019361919, dated May 21, 2024.

* cited by examiner

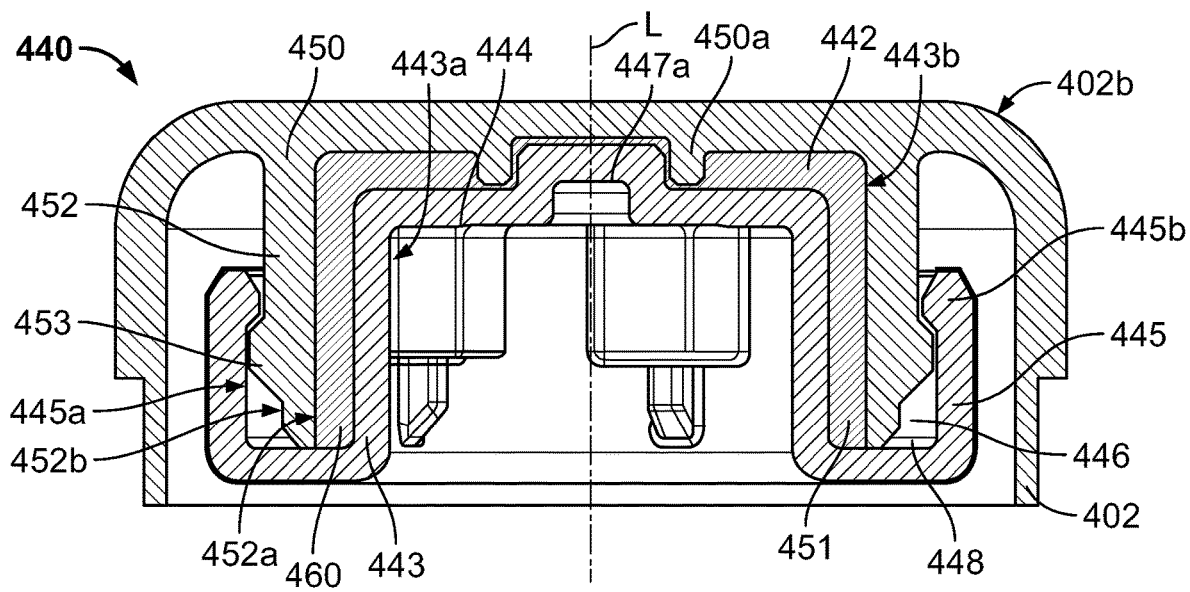
FIG. 5
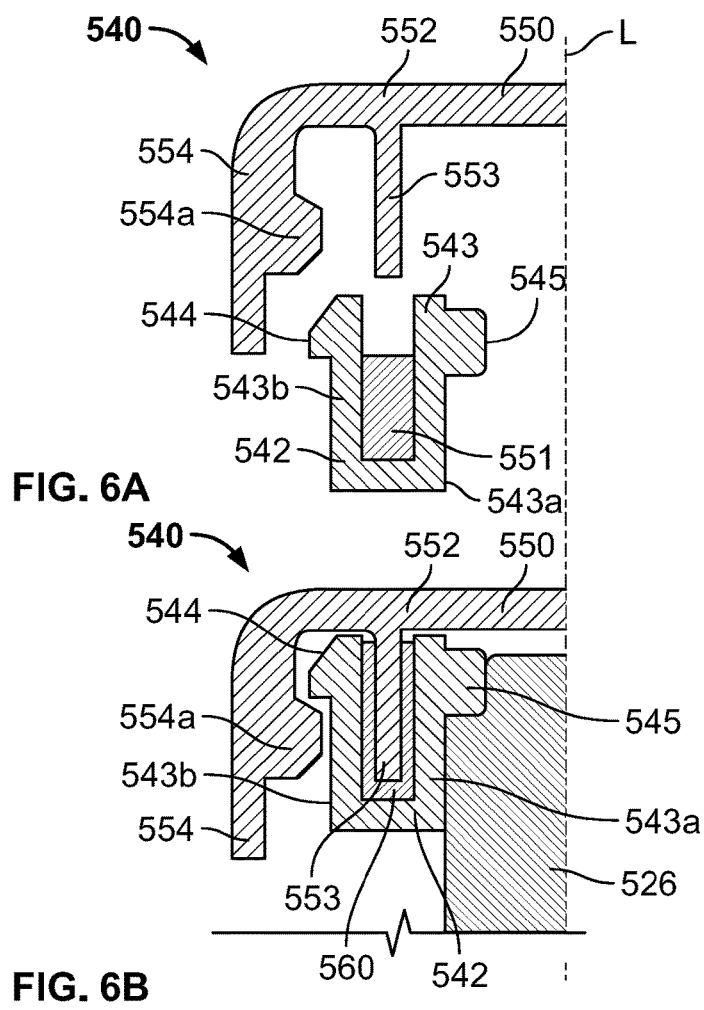
FIG. 6A
FIG. 6B

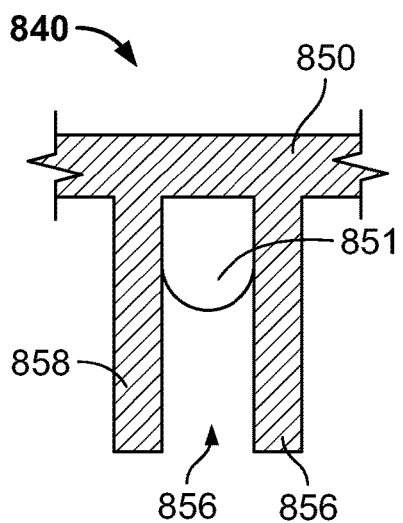
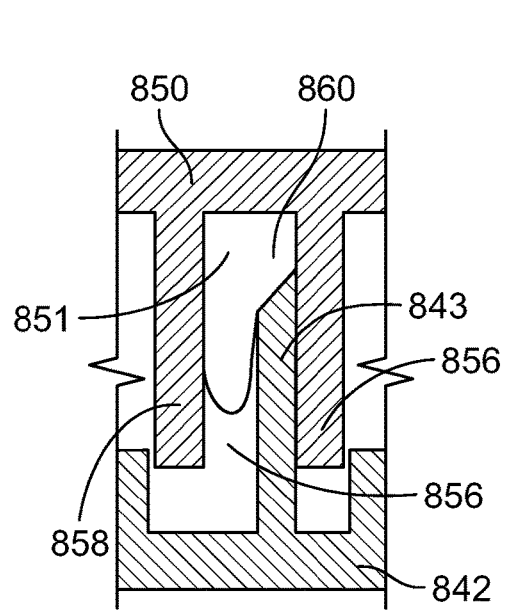
FIG. 9A        FIG. 9B
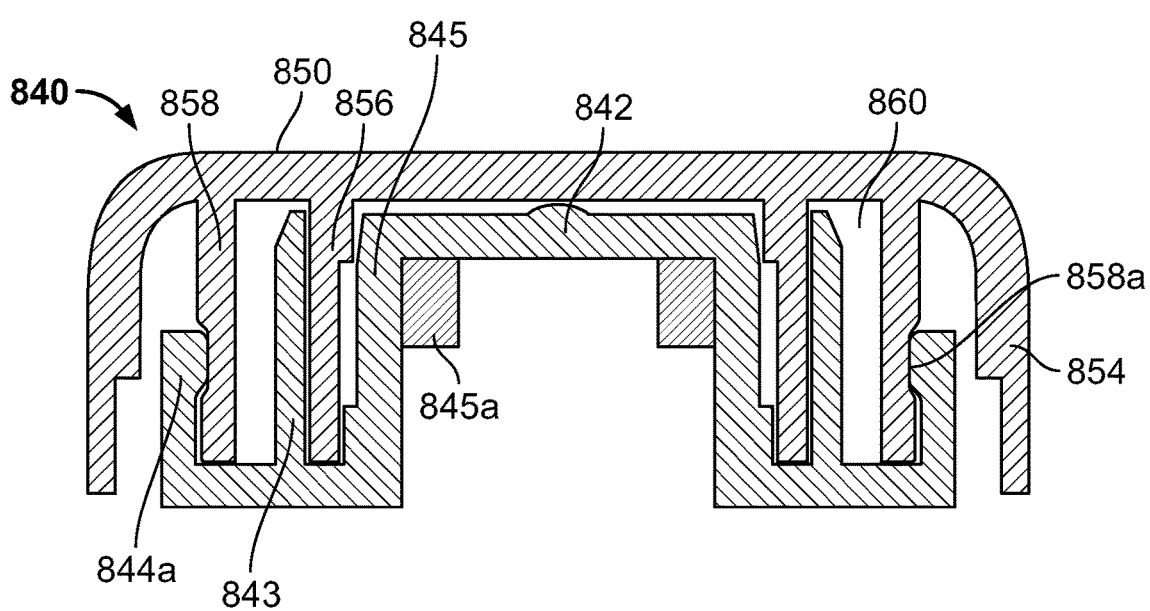
FIG. 9C

Nominal case

DRUG DELIVERY DEVICE HAVING DAMPING MECHANISM

CROSS-REFERENCE TO RELATED APPLICATION

Priority is claimed to U.S. Provisional Patent Application No. 62/745,813, filed Oct. 15, 2018, the entirety of which is hereby incorporated herein by reference.

FIELD OF DISCLOSURE

The present disclosure generally relates to injectors and, more particularly, to a torque driven injector having a damping mechanism.

BACKGROUND

Autoinjectors and on-body injectors offer several benefits in delivery of medicaments and/or therapeutics. One of the benefits can include simplicity of use, as compared with traditional methods of delivery using, for example, conventional syringes.

Many injector systems use coil spring structures to provide actuation energy for functions such as needle insertion and medicament delivery. The use of springs can offer benefits of simplicity for the user and device automation, but can have certain limitations. For example, there is a linear relationship between force and displacement in linear spring actuators. To provide sufficient energy for drug delivery at the end of plunger stroke, an excessive amount of energy may be input to the system as drug delivery commences.

Further, as higher viscosity drugs are delivered via autoinjectors, requisite spring forces will likely increase. Springs with higher spring constants transmit more force per travel distance to the drug product and primary container at the beginning of travel. In many autoinjectors, an air gap is present between a plunger face and a storage portion that contains the medicament prior to its injection into a user. When the drug is to be administered, the spring urges the plunger face through the air gap towards the medicament. Because the plunger face exhibits little resistance when traversing the air gap and due to large forces urging the plunger, the plunger face may make abrupt contact with the storage portion containing the medicament. A patient may feel this excessive energy as a "slap" or similar physical "bump", as the spring driven plunger impacts the stopper of the primary container storing the drug. Further, the user may also experience a jerk, recoil, and/or a reaction force when rotational movement begins due to the abrupt change in acceleration. Such mechanical bumps can be distracting and/or disturbing to users of the injectors and can therefore impact proper dose administration. Further, the "slap" and "bump" generated by the excessive energy can potentially cause catastrophic effects, such as breakage of the primary container and drug product damage cause by shear load. Furthermore, high force springs can produce undesirably high shear rates on the drug product.

Further still, patients may experience a large variation in injection times due to variations in characteristics of the medicament. These variations can be disturbing to users, who may think something is wrong with administration of the drug, and thus they may end the injection before they receive the full dosage. Variations in injection time may be caused by large drug viscosity variation due to changes to the temperature of the drug, large variations in friction between components in the device (e.g., between a syringe barrel and a stopper), and so on.

SUMMARY

In accordance with a first aspect, a drug delivery device includes a housing defining a shell having a proximal and a distal end, a needle assembly at least partially disposed within the housing at the proximal end, a drive assembly at least partially disposed within the housing, and a damper mechanism at least partially disposed within the housing at the distal end. The housing further defines a longitudinal axis extending between the proximal end and the distal end. The needle assembly includes a syringe barrel containing a medicament and a needle or a cannula. The drive assembly is operably coupled to the needle assembly to urge the medicament through the needle or cannula. The damper mechanism is operably coupled to the drive assembly and the housing. Upon activating the drive assembly, the damper mechanism dampens an effect thereof. In some examples, the syringe barrel may be constructed from a polymeric material. The medicament may have a viscosity of less than approximately 10 cP at approximately 21 degrees Celsius.

In this aspect, the damper mechanism includes a frame member, a damper member operably coupled to the drive assembly, a chamber formed between a portion of the frame member and the damper member, and a damper fluid disposed within the chamber. In some forms the frame member may be formed integrally with the housing. Upon activating the drive assembly of the drug delivery device, the frame member and the damper member rotate relative to each other, and the damper fluid exerts an opposing force on at least one of the frame member and the damper member.

In some approaches, the drug delivery device may also include an excess chamber fluidly coupled to the chamber. This excess chamber is adapted to receive excess damper fluid. Further, in some forms, the device may include a seal disposed near the chamber to retain the damper fluid within the chamber. In some aspects, the chamber is axially aligned with the longitudinal axis. In other approaches, the chamber may be partially axially aligned with the longitudinal axis and may be partially transversely aligned therewith. In yet other approaches, the chamber may be transversely aligned with the longitudinal axis.

In any of these examples, the drive assembly may include a plunger assembly including a threaded plunger rod and a plunger face, a plunger rod guide coupled to the plunger assembly, and a torque spring coupled to the plunger rod guide. The plunger face is disposed near the needle assembly and is movable along the longitudinal axis of the housing. The plunger rod guide guides rotational movement of the plunger assembly and is operably coupled to one of the frame member or the damper member. The torque spring exerts a force on the plunger rod guide that causes the plunger rod guide to rotate. Rotation of the plunger rod guide causes the plunger assembly to advance towards the proximal end of the housing to urge the medicament through the needle assembly. The plunger assembly may additionally include a clearance of greater than approximately 10 mm between the threaded plunger rod and the plunger face. Further, the syringe barrel may contain at least approximately 1 mL of medicament that has a viscosity of at least approximately 4 cP. Other examples are possible.

Further, in any of the foregoing examples, the damper mechanism can exert an opposing force on the drive assembly, or on at least one component operably coupled with the drive assembly.

In accordance with another aspect, a damper mechanism for a drug delivery device includes a frame member, a damper member operably coupled to a drive assembly of the drug delivery device, a chamber formed between a portion of the frame member and the damper member, and a damper fluid disposed within the chamber. Upon activating the drug delivery device to administer a medicament to a user, the frame member and the damper member rotate relative to each other and the damper fluid exerts an opposing force on at least one of the frame member and the damper member.

In accordance with yet another aspect, an autoinjector includes a housing defining a shell having a proximal end, a distal end, and a longitudinal axis extending therebetween, a needle assembly at least partially disposed within the housing at the proximal end thereof, and a drive assembly at least partially disposed within the housing. The needle assembly includes a syringe barrel containing a medicament and a needle or a cannula. The drive assembly is operably coupled to the needle assembly to urge the medicament through the needle or cannula. The drive assembly includes a plunger assembly having a plunger rod and a plunger face being disposed near the needle assembly and being moveable along the longitudinal axis of the housing. The syringe barrel is adapted to contain at least approximately 1 mL of medicament having a viscosity of at least approximately 4 cP. The plunger rod and the plunger face have an initial clearance of greater than approximately 10 mm.

BRIEF DESCRIPTION OF THE DRAWINGS

The above needs are at least partially met through provision of the torque driven drug delivery device described in the following detailed description, particularly when studied in conjunction with the drawings, wherein:

FIG. 5 illustrates a cross-sectional view of a fourth example damper mechanism of a drug delivery device in accordance with various embodiments;

FIGS. 6a and 6b illustrates cross-sectional views of a fifth example damper mechanism of a drug delivery device in accordance with various embodiments;

FIGS. 9a-9c illustrate cross-sectional views of an eighth example damper mechanism of a drug delivery device in accordance with various embodiments;

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments, a torque driven injector includes a housing, a syringe assembly containing a medicament to be injected into a user, and a rotatable actuating assembly using a torque spring to cause the medicament to be injected into the user. As the rotatable actuating assembly rotates to cause the drug to be administered, a fluid damper is used to provide a more consistent drug delivery time between drugs of varying viscosities, as well as drugs that may exhibit changes in viscosity based on different environmental changes (e.g., varying temperatures).

Further, as the actuating mechanism rotates, the damper mechanism can reduce or eliminates the "slap" or "bump" that occurs when the plunger face first contacts the medicament and/or medicament storage device. The damper mechanism may also reduce the "jerk" or recoil when the mechanism is released. Accordingly, a user will not feel this sudden movement during the drug delivery process, and can comfortably and safely administer the medicament. Further, the torque spring, which uses a high number of turns, discussed in further detail below, may maintain near-constant start and end torque as compared to traditional springs and those with fewer turns. As a result, smaller autoinjectors may be used, which can increase overall user comfort. Additionally, the damper may reduce and/or eliminate the variation in injection times and minimize the risk of the device stalling. The damper may also provide for design freedom to target optimal injection times for usability, and can potentially eliminate the need to customize the device for different drug volumes.

Figures 1, 2:
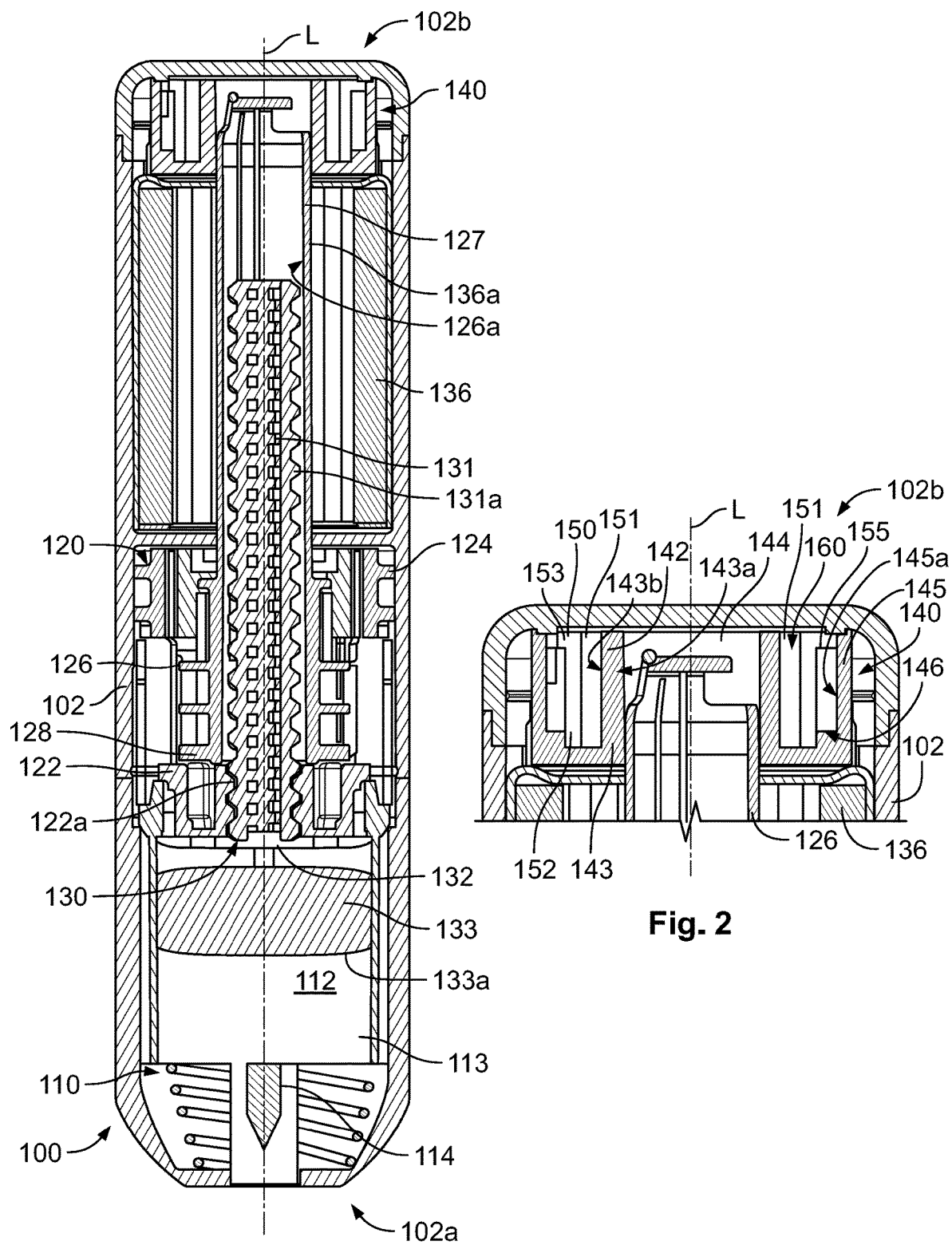
FIG. 1 illustrates a cross-sectional view of an example torque driven drug delivery device having a damper mechanism in accordance with various embodiments.
FIG. 2 illustrates a close-up cross-sectional view of the damper mechanism of the example drug delivery device of FIG. 1 in accordance with various embodiments.

Referring now to the drawings, and in particular to FIGS. 1 and 2, an example autoinjector 100 includes a housing 102 defining a shell, a needle assembly 110 at least partially disposed within the shell 102, a drive assembly 120 also at least partially disposed within the shell 102, and a damper mechanism 140 at least partially disposed within the shell 102. The shell 102 includes a proximal end 102a, a distal end 102b, and defines a longitudinal axis "L" extending between the proximal end 102a and the distal end 102b.

The needle assembly 110 is generally disposed at or near the proximal end 102a of the shell 102 and includes a syringe barrel 112 containing a medicament 113 and a needle or a cannula 114. The needle assembly 110 may include any number of additional components such as, for example, a sidewall or sidewalls, openings to allow the medicament 113 to pass to the needle or cannula 114, return springs, shield members, filter members, and the like, but for the sake of brevity, will not be discussed in substantial detail. A portion of the syringe barrel 112 may be open to accommodate a portion of the drive assembly 120, which will be described in further detail below. The syringe barrel 112 may be of any desired shape and/or size to accommodate various quantities of medicament 113. In some examples, the syringe barrel 112 can be constructed from a polymeric material such as cyclic-olefin polymer ("COP"), cyclic olefin copolymer ("COC"), or a glass material. Other examples are possible.

The drive assembly 120 may include a nut 122 positioned adjacent to the syringe barrel 112, a trigger ring 124, a plunger rod guide 126, a plunger rod assembly 130, and a drive mechanism in the form of a torque or power spring 136. Generally, portions of the drive assembly 120 may be fixedly coupled to the shell 102 via any number of approaches. In some arrangements, the nut 122 may be formed integrally with the shell 102 and may include a threaded opening 122a. The trigger ring 124 selectively engages the nut 122 and is configured to move in an axial direction. In the illustrated example, the trigger ring 124 is in the form of a generally cylindrical ring having a generally circular inner surface and any number of ledges, protrusions, and grooves disposed around and/or inside the circumference of the ring. The trigger ring 124 may be coupled to the housing 102 via any number of techniques.

The plunger rod guide 126 includes a rod portion 127 and a base portion 128 coupled thereto. The plunger rod guide 126 includes an opening 126a extending at least partially through the rod portion 127 and the base portion 128. The base portion 128 can have any number of projections or tabs extending therefrom to define a slidable engagement with the trigger ring 124.

The plunger rod assembly 130 includes a plunger rod 131, a washer 132, and a plunger 133 that are moveable along the longitudinal axis L of the housing 102. The plunger rod 131 has a threaded portion 131a which is threadably coupled to the plunger rod guide 126 and the threaded opening 122a of the nut 122. The washer 132 minimizes frictional losses between rotation of the plunger rod 131 and the non-rotating plunger 133. In some approaches, the washer 132 may also be used to adjust the volume of medicament 113 by making the washer 132 thicker or narrower. Accordingly, the washer 132 may be used to accommodate a range of fill volumes of medicament 113 in the same device 100, thereby allowing for better control of the air gap between the bottom of the washer 132 and the top of the plunger 133.

The rod portion 127 of the plunger rod guide 126 is coupled to the plunger rod assembly 130 via any number of approaches including, for example, via a splined connection or slotted arrangement that allows for the plunger rod assembly 130 to be axially displaced relative to the plunger rod guide 126. As such, the plunger rod guide 126 guides rotational movement of the plunger rod assembly 130. The threaded portion 131a of the plunger rod 131, and correspondingly, the threaded opening 122a of the nut 122 may have a thread pitch suitable for any desired drug delivery rate or force/torque combination when driven by the drive mechanism 136. Relative rotation between the plunger rod 131 and the nut 122 causes the plunger rod 131 to advance axially towards the proximal end 102a of the housing 102. The plunger 133 has a top face 133a that is disposed near the syringe barrel 112.

In the illustrated example, the drive mechanism 136 is in the form of a power spring or a torque spring 136 having an inner portion 136a coupled to the rod portion 127 of the plunger rod guide 126 via any known approach to exert a torque on the plunger rod guide 126 that causes the plunger rod guide 126 to rotate about axis L. In some examples, the torque spring 136 may have a high number of turns to provide an appropriate rotational travel required to expel the medicament from the syringe barrel 112, however, additional parameters of the spring design may influence its torque output such as material properties and any applied heat treatments. The pre-shaping of the torque spring 136 may also impact its performance. As an example, in an autoinjector, a pre-stressed spring may be preferred, because the pre-stressing process generally increases torque output of the spring by initial coiling the spring in an opposite direction of the intended working condition, thereby causing permanent deformation in the steel band. This deformation maximizes the stresses in the material, thereby causing the torque to increase. Such an increase in torque is beneficial to minimize device size and weight.

In some examples, the torque spring 136 may have between approximately 1 and approximately 30 turns in the wound or loaded configuration, and preferably, approximately 12 turns. In some examples, the total spring turns may be higher due to a margin in both ends of the working range of approximately 20%, which may result in the range being between approximately 1*1.4=1.4 to 30*1.4=42. The dose mechanism turns are derived from the pitch and the required travel length. As previously stated, a smaller pitch is preferred due to requiring a low torque input and activation force. Accordingly, the activation force also will be lower. If a high axial force is not needed, the pitch can be raised and require fewer spring turns, thus allowing the device to be smaller. In some examples, the torque spring 136 may have a number of initial or preload turns to have a usable torque. After the preload turns, the torque spring 136 is further wound with working turns, or turns that are used in the device during injection. As a non-limiting example, the torque spring 136 may have approximately 2.5 preload turns and approximately 6 working turns. As such, the total number of turns during assembly is approximately 8.5. However, due to potentially large tolerances in the angular positioning of spring terminations, the torque spring 136 may have an initial play before reaching a solid state, and thus may have a total of approximately 10 turns. Devices having different drug volumes and viscosities may need a different average torque generated from the torque spring 136 if the same dosing is desired. The average torque output may be controlled by adjusting the width of the band used for the torque spring 136 (e.g., the axial length of the torque spring 136 when disposed in the device), and maintaining the same number of working turns. Doing so may allow different springs to be used with the same configuration as the device and have similar injection times while the volume and/or viscosity of the drug may be modified.

In some examples, the energy (EFLOW) required to expel the medicament 113 through a needle 114 is determined by any combination of the drug volume, viscosity, needle flow path dimensions, and the targeted dosing time. The energy (ESPRING) that the torque spring 136 delivers may be determined by any combination of the number of working turns (N) and the average spring torque during the working turns (T). The energy delivered by the spring may be calculated using the following formula: ESPRING=2*π*N*T. If frictional losses are excluded in the system, the following relationship exists: EFLOW=ESPRING=2*π*N*T. Accordingly, the following relationship results: EFLOW/(2*π)=N*T. In other words, to have sufficient energy in the torque spring 136 to expel a given drug in a given volume through a given needle in a given time, the product (N*T) remains constant, and thus the higher torque may be converted to fewer working turns.

The threaded interface between the plunger rod 131 and the nut 122 provides a translation between the input torque of the torque spring 136 and the output axial force. By providing a torque spring 136 with a high turn count, it will have a lower overall torque as well as a smaller change in start and end torque as compared to a linear spring having comparable gearing specifications or other torsion springs with few turns and a lower pitch. Additionally, the threads of the plunger rod 131 and the nut 122 can have a lower pitch due to the increase in turn count, while still achieving the same linear motion of the plunger rod assembly 130. If the thread pitch is low, a smaller input torque is necessary to provide the same output force as a high pitch thread and high torque spring. Accordingly, the high turn count (e.g., between approximately 1 and approximately 30 turns), low torque system described herein allows for reduced activation forces, as the activation force is directly related to the input torque that must be used to drive the plunger rod assembly 130. Additionally, internal structural forces required to resist the torque from the torque spring 136 during storage (e.g., prior to use) is reduced, thus allowing for smaller injector designs to be used and for less expensive raw materials to be used. Additionally, the threaded interface between the plunger rod 131 and the nut 122 allows the threaded plunger rod 131 to be adjusted to accommodate for varying quantities of medicament stored in the syringe barrel 112. If necessary, the threaded plunger rod 131 may be initially installed at a lower position in injectors 100 having lesser drug product volumes disposed in the syringe barrel 112. Accordingly, the number of unique components is reduced, and variation management is simplified. The threaded plunger rod 131 may also be adjustably installed at various depths during the manufacturing and/or assembly process as needed.

The damper mechanism 140 is also at least partially disposed within the housing 102 at the distal end 102b thereof. The damper mechanism 140 is operably coupled to a portion of the drive assembly 120 (e.g., the plunger rod guide 126) and the housing 102. The damper mechanism 140 acts to dampen the effect of the torque spring 136 on the drive assembly 120.

Generally, to activate the device, a user presses the device 100 against their skin, thereby causing the trigger ring 124 to disengage from the nut 122 and/or the plunger rod guide 126. Such disengagement allows the plunger rod guide 126 to rotate relative to the trigger ring 124. Because the torque spring 136 is in a wound or compressed state, the torque spring 136 will begin to unwind, thereby causing the plunger rod guide 126 to rotate. This rotation in turn causes the plunger rod 131 to rotate, which, due to the threaded interface between the plunger rod 131 and the nut 122, causes the plunger rod 131 and the plunger 133 to advance towards the proximal end 102a of the housing 102, thereby inserting the needle or cannula 114 and administering the medicament 113. As a non-limiting example, U.S. Provisional Application No. 62/719,367, filed on Aug. 17, 2018, describes an activation process and components of the drive assembly in further detail and accordingly is incorporated by reference herein in its entirety.

In the illustrated example of FIGS. 1 and 2, the damper mechanism 140 includes a damper member 142, a frame member 150, a chamber 160 formed between a portion of the damper member 142 and the frame member 150, and a damper fluid 151 disposed within the chamber 160. The damper member 142 may be coupled to the plunger rod guide 126 via any number of approaches such as, for example, via a friction fit or threaded engagement. The damper member 142 includes a body 143 having an inner surface 143a that defines a central opening or bore 144 to accommodate a portion of the plunger rod guide 126, and further includes an outer surface 143b. The damper member 142 further includes a winged portion 145 having an inner surface 145a positioned away from the body 143 that faces the outer surface 143b thereof. A channel 146 is formed between the outer surface 143b of the body 143 and the inner surface 145a of the winged portion 145.

The frame member 150 is operably coupled to the housing 102. For example, the frame member 150 may be in the form of a cylindrical member defining a body 152 and a coupling portion 153 to couple to the housing 102 via any number of approaches such as, for example, adhesives, threaded, frictional connections, and the like. In some examples, the frame member 150 may be integrally formed with the distal end 102b of the housing 102.

The body 152 of the frame member 150 is adapted to be at least partially inserted into the channel 146 of the damper member 142. In the illustrated example, the frame member 150 further includes a ledge 155 that engages (e.g., via a frictional connection) the inner surface 145a of the winged portion 145. The chamber 160 is defined by the body 152 of the frame member 150 and the body 143 of the damper member 140. In some examples, the shell 102 may further define an end surface of the chamber 160. The damper fluid 151 is disposed within this chamber 160.

As previously mentioned, relative rotation between components of the damper mechanism 140 causes the damper fluid 151 to dampen this effect. Specifically, in this example, the damper member 140 rotates relative to the frame member 150 when the plunger rod guide 122 rotates. A torque from the torque spring 136 exists between the damper member 142 and the frame member 150, thereby causing the system to accelerate from rest thus increasing speed. During relative rotation, the damper fluid 151 experiences shear stress due to rotation of the damper member 142. In the disclosed example, the damper fluid 151 thus exerts an opposite acting reaction torque on the drive assembly 120 and, in particular, the plunger rod guide 126 of the drive assembly 120. The speed of the drive assembly 120 increases until the opposite acting damper torque has been built up to the same level as the dosing torque and equilibrium is reached. This equilibrium occurs at a specific speed and torque, and is dependent on a number of factors such as, for example, geometry of the damper mechanism 140, fluid properties of the damper fluid 151, and the torque profile of the torque spring 136. Other examples are possible.

Figure 21:
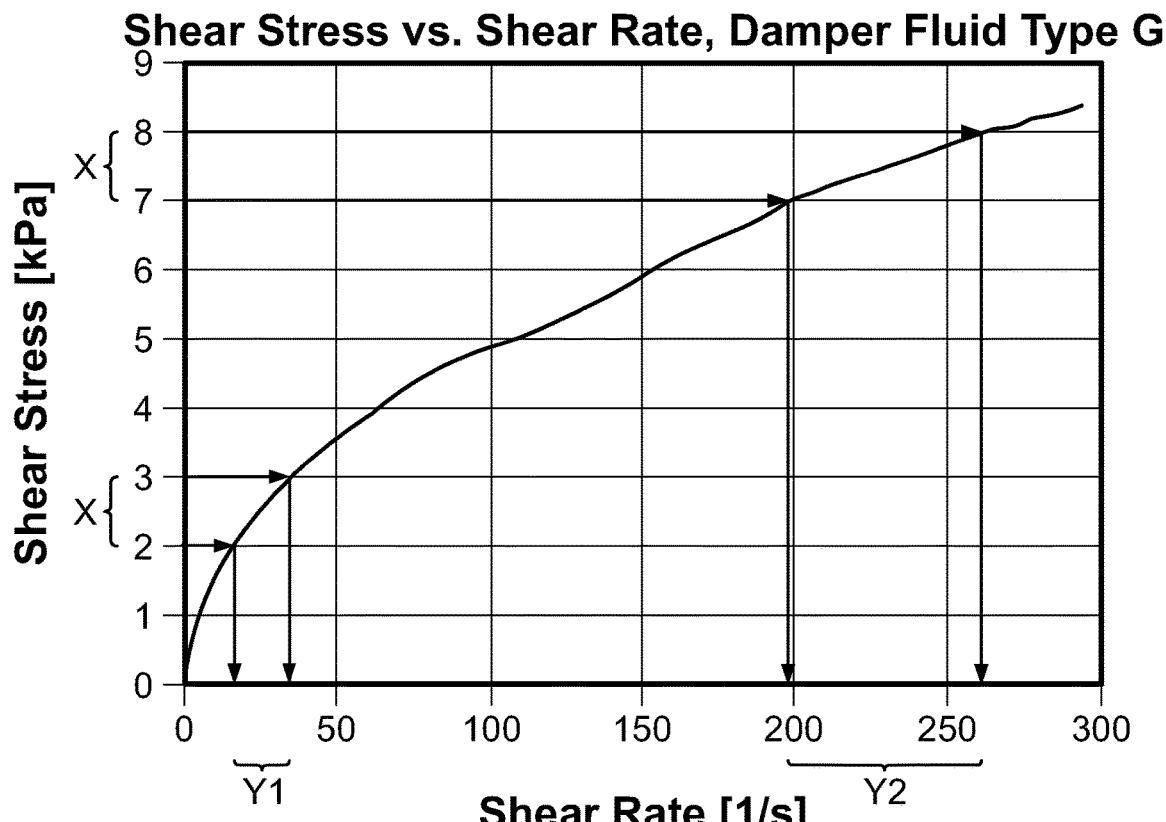
FIG. 21 illustrates a graph depicting shear stress as a function of shear rate in accordance with various embodiments.
Figure 22:
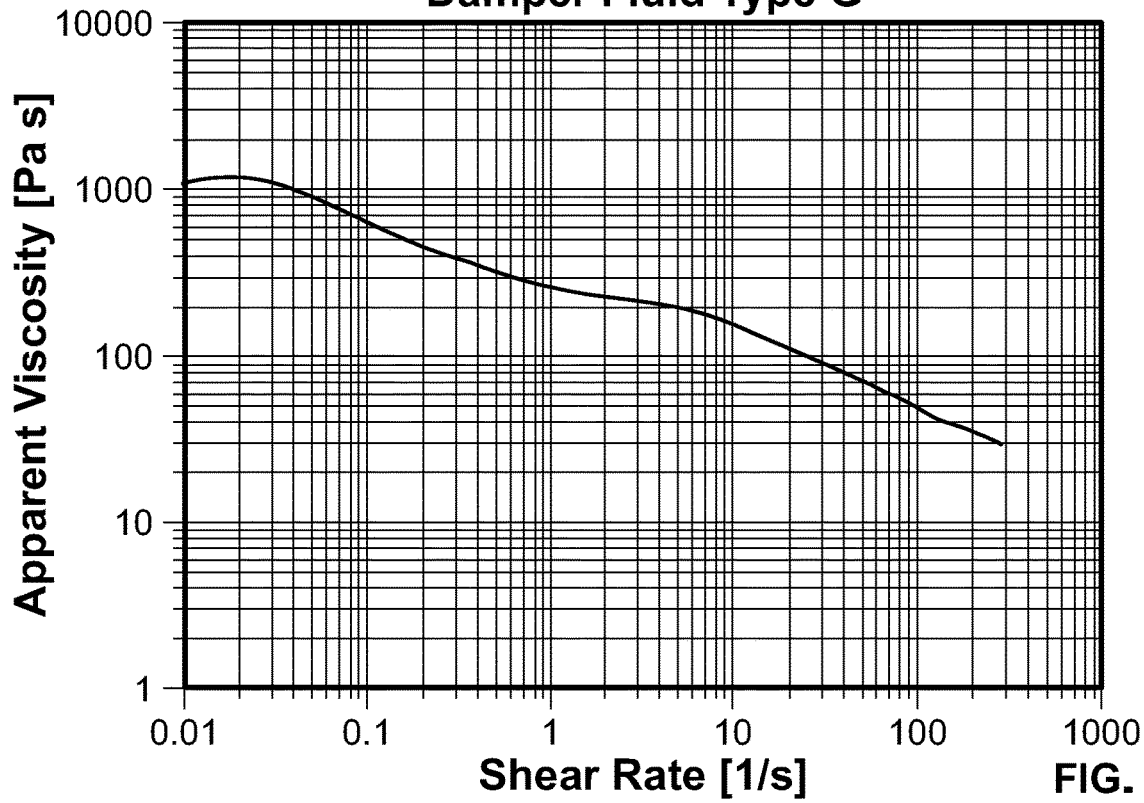
FIG. 22 illustrates a graph depicting apparent viscosity as a function of shear rate in accordance with various embodiments.

So configured, the damper mechanism 140 has a relatively simple design using minimal parts to reduce assembly and component costs and complexity. The damper mechanism 140 may be easily assembled, filled, and tested on a separate assembly line prior to being inserted into the device 100. In some examples, it may also be of interest to have a robust and stable damper mechanism 140. There are a number of parameters that may affect the performance of the damper mechanism 140, and by reducing the influence of these parameters may further increase the stability of the damper mechanism 140. For example, and as previously noted, a damper fluid 151 having a low variation in viscosity as a function of temperature may be selected that have shear thinning properties. The shear stress in the damper fluid 151 is directly related to the damping torque. To obtain a relative constant and predictable speed at a certain needed damping torque, it is desired to have a change in input torque (and thereby shear stress) cause a minimal change in shear rate. In some examples, and as illustrated in FIG. 21 that depicts shear stress as a function of shear rate for a damper fluid type "G", this may be best obtained by having a design with a shear rate in the lower end, as the variation in shear rate, y, at a given input torque interval is less in this area. It is noted that the provided curve in FIG. 21, and the values illustrated therein, only represent an example curve, and accordingly other curves may be used. FIG. 22 illustrates the apparent viscosity of the damper fluid type G. The shear thinning properties can be seen by the decrease in the apparent viscosity with the increase in shear rate.

Another parameter that may impact robustness and stability of the damper mechanism include a large gap at a small diameter. The shear rate level is designed to and influenced by the dimensions of the damper mechanism 140. The size of the gap that defines the chamber 160 impacts the shear rate. The art tolerances can impact the size of the chamber 160 the least amount if the nominal chamber 160 size is as large as possible and if the chamber 160 is placed at the smallest possible diameter.

Figure 23:
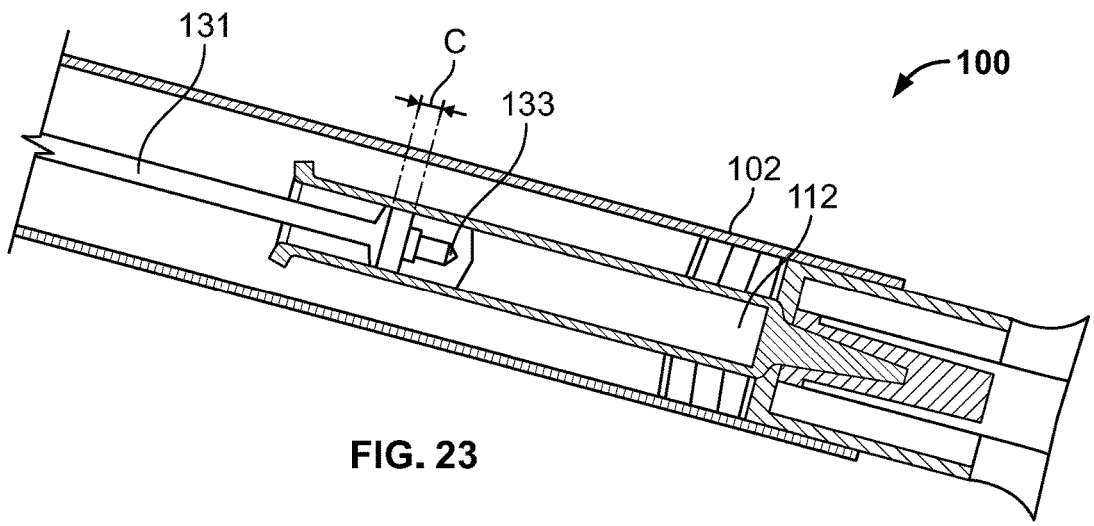
FIG. 23 illustrates a perspective view of an example drug delivery device having a clearance between components in accordance with various embodiments.

Further, with brief reference to FIG. 23, the described damper mechanism 140 may allow for significant clearances "C" (e.g., approximately 10 mm or more) between the plunger rod 131 and the plunger 133 without risking breakage of the syringe barrel 112 or other components of the device 100 upon its activation and upon impact between the plunger rod 131 and the plunger 133. These devices may be adapted to extrude at least approximately 1 ml of medicament 113 having a viscosity of at least approximately 4 cP. Such large clearances advantageously reduce platform complexity, inventory variations, and/or process controls. The damper mechanism 140 also provides for a better user experience when compared to devices without a damper mechanism, where the impact shock, feel, and sound may startle a user.

Figure 3:
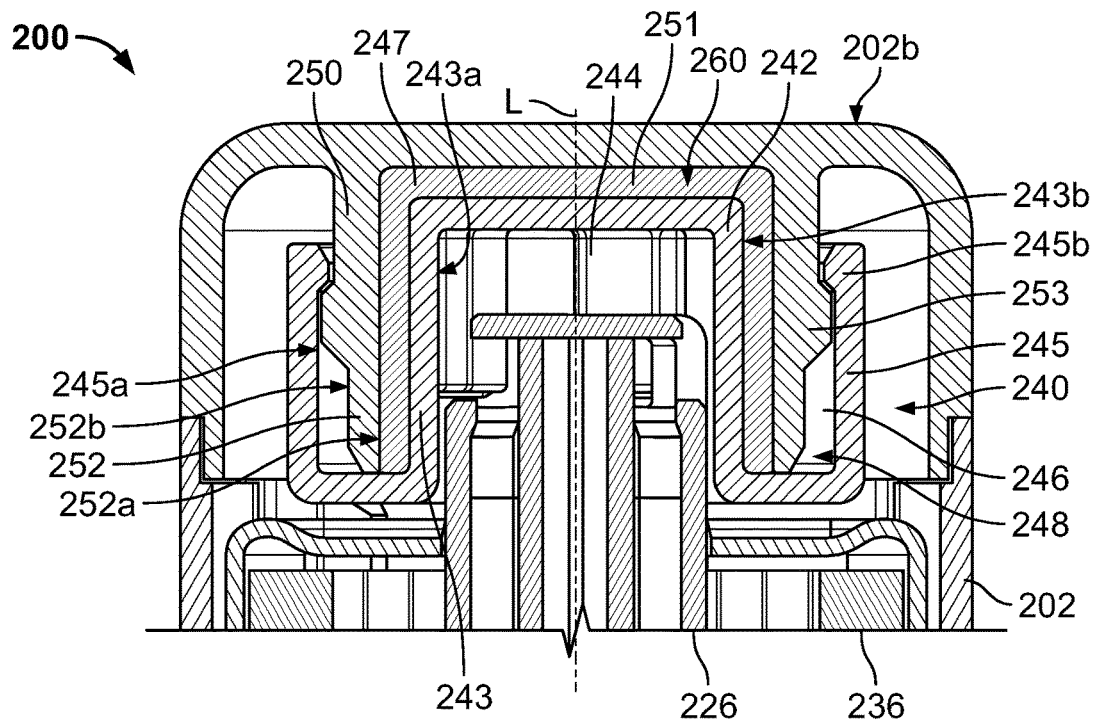
FIG. 3 illustrates a cross-sectional view of a second example drug delivery device having a chamber for excessive damper fluid in accordance with various embodiments.

In some examples, it may be beneficial for a substantial surface of the damper member to be in contact with the damper fluid. If the entire surface is not in contact with the damper fluid due to under filling, the damping torque will be reduced. Accordingly, FIG. 3 illustrates an alternative damper mechanism 240 for a drug delivery device 200 that is less sensitive to the filling precision. It will be appreciated that the drug delivery device 200 includes any number of similar components and/or features as the drug delivery device 100, and thus includes similar two-digit suffixes as used with reference to FIGS. 1 and 2. Accordingly, these components will not be discussed in substantial detail. In the drug delivery device 200, the damper member 242 includes a body 243 having an inner surface 243a defining a central opening or bore 244 to accommodate a portion of the plunger rod guide 226, and further includes an outer surface 243b. The damper member 242 includes a winged portion 245 having an inner surface 243a and a notch 245b. The damper member 242 further defines a channel 246 between the outer surface 243b of the body 243 and the inner surface 243a of the winged portion 245, and further includes an end cap portion 247.

In this example, the frame member 250 is integrally formed as an end cap of the housing 202. The frame member includes a generally cylindrical protrusion 252 having an inner surface 252a and an outer surface 252b. The cylindrical protrusion 252 defines a tab 253 on the outer surface 252b. When the damper mechanism 240 is installed onto the drug delivery device 200, the cylindrical protrusion 252 is inserted into the channel 246. In this configuration, the notch 245b engages the tab 253 to restrict relative axial movement between the damper member 242 and the frame member 250. Further, the concentric cylinders are constrained to each other in a radial direction so part tolerances have minimal influence on concentricity. However, relative rotation between the damper member 242 and the frame member 250 is still permitted. In this example, a U-shaped chamber 260 is formed between the protrusion 252, the body 243, and the end cap portion 247 to accommodate the damper fluid 251. In such a configuration, the chamber is partially axially and partially transversely aligned with the longitudinal axis L. When constructed, the channel 246 further defines an excess chamber 248 to accommodate any excess damper fluid, which may be used to selectively adjust the damping torque generated, or may simply be used as a "spillover" region if more fluid than desired was inadvertently supplied. In these examples, the damper mechanism 240 may engage the housing 202 and/or the drive assembly 220 as desired. Further, the damper mechanism 240 may be assembled to the device 200 via an axial assembly process.

Figure 4:
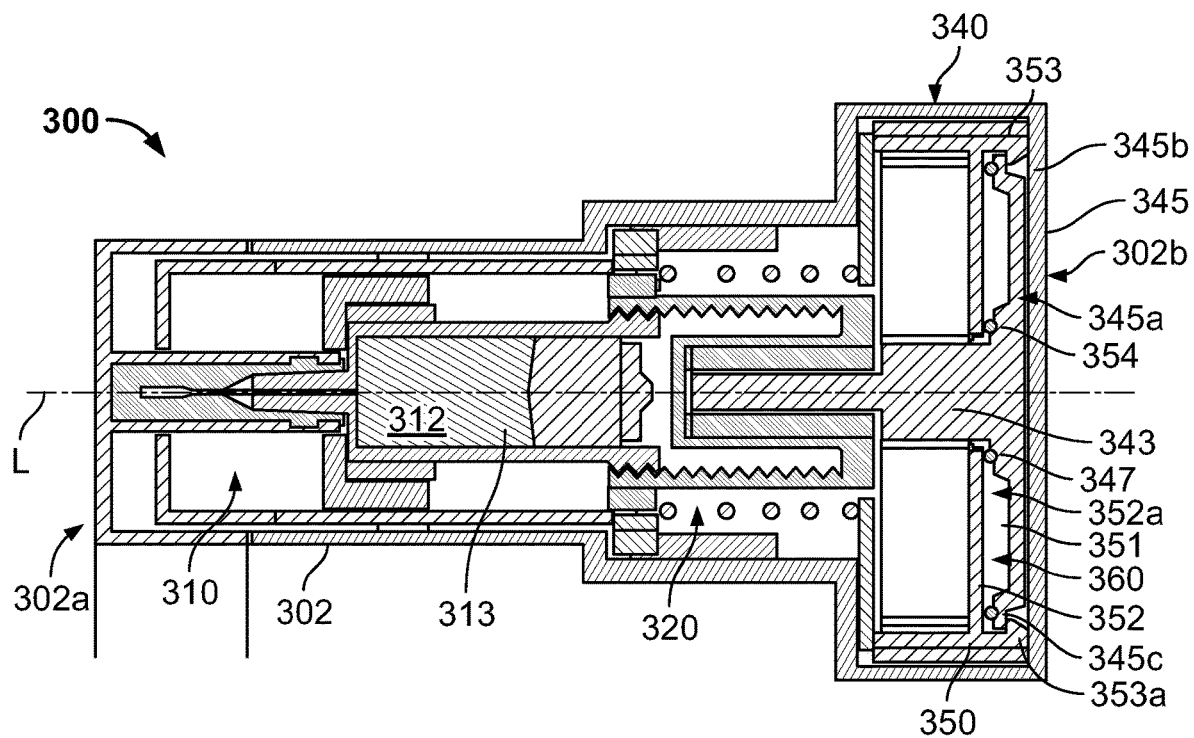
FIG. 4 illustrates a cross-sectional view of a third example drug delivery device having a damper fluid disposed between disks of the damper mechanism in accordance with various embodiments.

In some examples, it may be desired to provide a sealing portion to ensure the damper fluid stays in the desired chamber in order to maintain a consistent damping torque. Such a seal may create a resistance force between the frame and the damper member, which in turn will create a resistance torque. This may be undesirable during dosing as the power source (i.e., the torque spring), may need to be larger to overcome this extra resistance. Accordingly, FIG. 4 illustrates an alternative drug delivery device 300 having an alternative damper mechanism 340 that allows for simple filling of the damper fluid, while preventing the fluid from escaping. The drug delivery device 300 includes any number of similar components and/or features as the drug delivery devices 100 and 200, and thus includes similar two-digit suffixes as used with reference to FIGS. 1-3. Accordingly, these components will not be discussed in substantial detail. In the drug delivery device 300, the damper member 342 includes a body 343 and a disk portion 345 coupled to the body 343. The disk portion 345 defines a first surface 345*a* and includes any number of grooves 345*b* positioned along its length and terminates at an outer end 345*c*. The frame member 350 is also in the form of a generally cylindrical member having a generally disk-like base 352 defining a first surface 352*a* and a sidewall portion 353 that includes a tab 353*a*. The disk-like base 352 further defines an opening 354.

In the illustrated example, any number of sealing members 347 are disposed within or adjacent to the groove or grooves 345*b* of the damper member 342. To assemble the damping mechanism, the disk damper member 342 is inserted into the opening 354 of the base 352, whereby the outer end 345*c* engages the tab 353*a* of the sidewall portion 353. As a result, a chamber 360 is formed between the first surface 345*a* of the disk portion 345 and the first surface 352*a* of the base 352. In this example, the chamber 360 is disposed in a transverse configuration, and is sealed off via sealing member(s) 347. Such a damper mechanism 340 can be assembled in the same power module in which no internal rotary play exists, thereby reducing and/or eliminating risk of the device 300 jerking at activation.

Turning to FIG. 5, an alternative damper mechanism 440 for a drug delivery device 400 includes similar features as the previously described damper mechanism 240. Accordingly, these features have similar two-digit suffixes as those provided in FIG. 3, and thus will not be described in substantial detail. The damper mechanism 440 additionally includes a generally cylindrical extension 447*a* extending from the end cap portion 247 that mates with an inner cylinder 450*a* extending from the frame member 450. When the frame member 450 and the damper member 442 are coupled together, relative rotation is still permitted, but the concentric engagement between the extension 447*a* and the inner cylinder 450*a* provides for increased centering of the components, thereby resulting in a smaller variance of chamber 460 size.

Turning to FIGS. 6*a*-8, alternative damper mechanisms are provided that effectively double the damping surface by creating two chambers that accommodate damping fluid on multiple sides of a frame member. As a result, these damping mechanisms may create approximately double the damper torque as compared to a similar design having a single chamber. Advantageously, these damper mechanisms may be made smaller compared to the single chamber design if the same level of damping torque is needed. These damping mechanisms include similar features as those described with reference to FIGS. 1-5, and thus include similar two-digit suffixes. Accordingly, for the sake of brevity, some of these components may not be described in substantial detail.

As illustrated in FIGS. 6*a* and 6*b*, the damper member 542 is generally U-shaped and defines a channel 546 between an inner sidewall 543*a* and an outer sidewall 543*a* The damper member 542 may additionally include a tab 544 extending from the outer sidewall 543*b*, and a ledge 545 extending from the inner sidewall 543*b*, The frame member 550 includes a base portion 552, a first generally cylindrical protrusion 553, and a second generally cylindrical protrusion 554 that carries a notch 554*a*.

In operation, the ledge 545 of the damper member 542 frictionally engages the plunger rod guide 526 to be rotatably coupled thereto. The channel 546 is filled with damper fluid 551, and the frame member 550 is coupled to the damper member 542 by inserting the first cylindrical protrusion 553 into the channel 546. Upon doing so, the notch 554*a* engages the tab 544 to secure the damper member 542 to the frame member 550. Further, the first cylindrical protrusion 553 segments the channel 546 into a U-shaped chamber 560 whereby the damper fluid 551 surrounds the first protrusion 553 and thus is disposed on both sides thereof.

Figure 7:
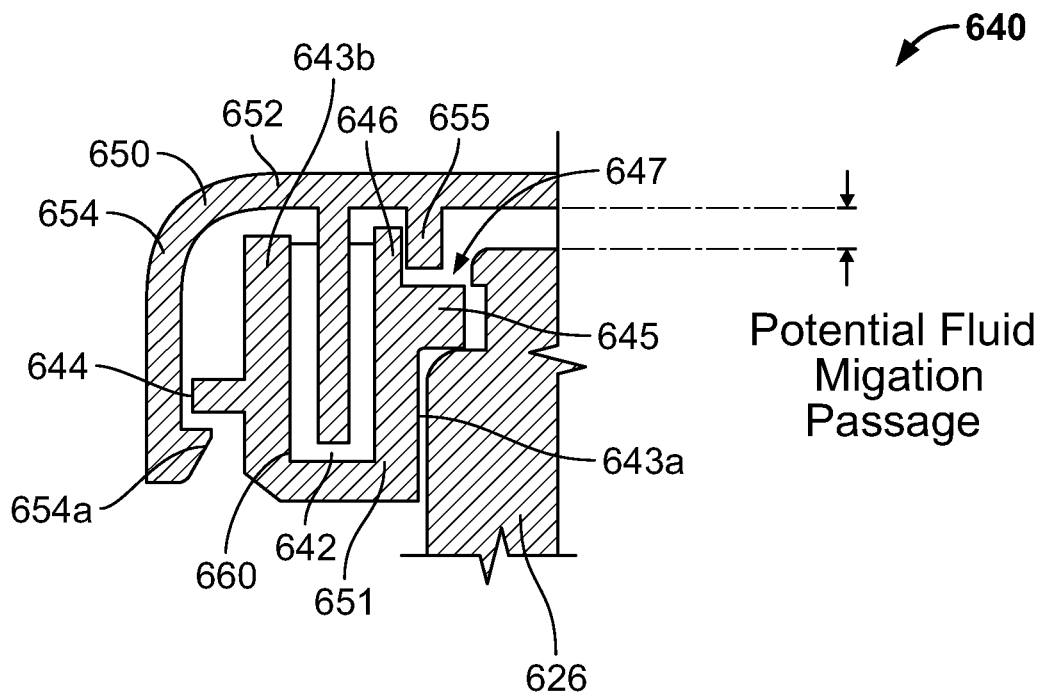
FIG. 7 illustrates a cross-sectional view of a sixth example damper mechanism of a drug delivery device in accordance with various embodiments.
Figure 8:
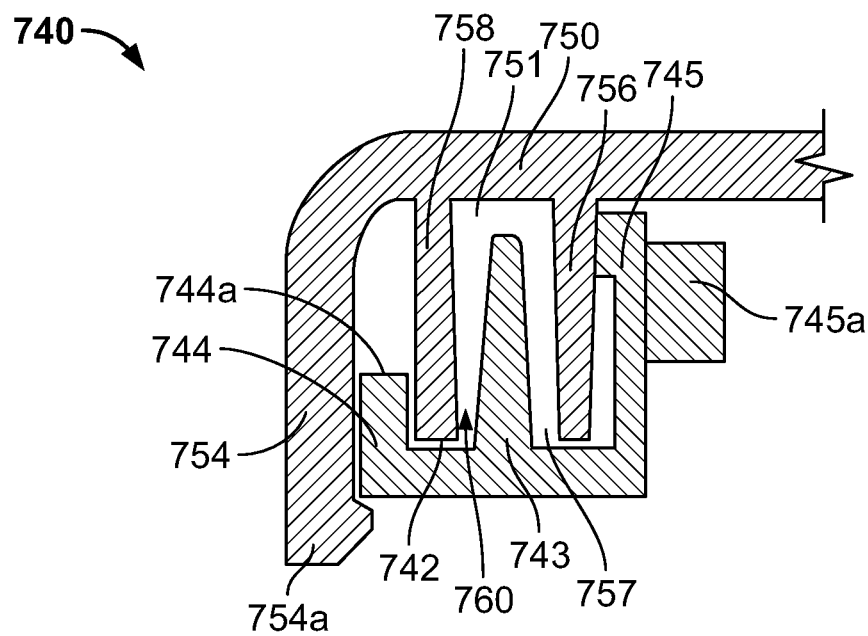
FIG. 8 illustrates a cross-sectional view of a seventh example damper mechanism of a drug delivery device in accordance with various embodiments.

FIG. 7 illustrates a similar damper mechanism 640 as the mechanism 540 described in FIGS. 6*a* and 6*b*, but additionally includes a third generally cylindrical protrusion 655. This protrusion 655 engages the inner sidewall 643*a* to create an additional channel 647 which acts as a fluid mitigation passage. In FIG. 8, the components in the damper mechanism 740 are essentially reversed. In other words, the frame member 750 defines a channel 757 between a first sidewall 756 and a second sidewall 758, while still including a cylindrical protrusion 754 that carries a notch 754*a*. The damper member 742 includes a first protrusion 743, a second protrusion 744 carrying a tab 744*a*, and a third protrusion 745 carrying a ledge 745*a*. The damper fluid 751 is disposed within the channel 757, and the first protrusion 743 is inserted therein to define the chamber 760 that surrounds the first protrusion 743.

Figure 10:
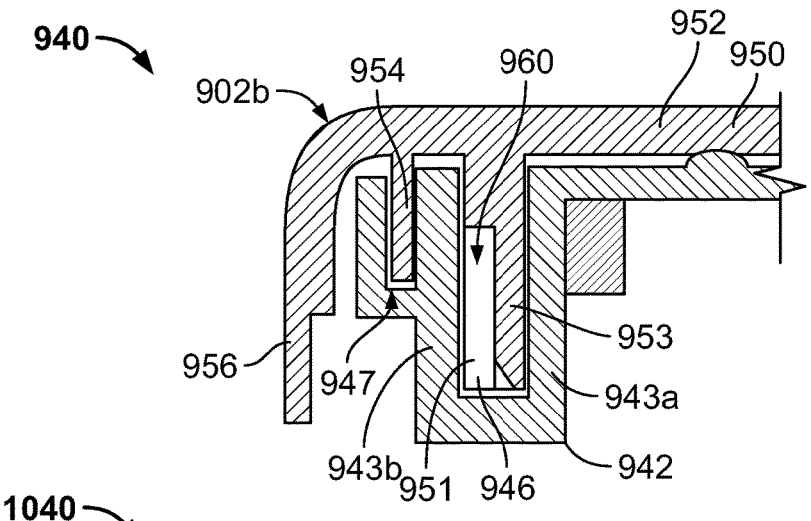
FIG. 10 illustrates a cross-sectional view of a ninth example damper mechanism of a drug delivery device in accordance with various embodiments.

FIGS. 9*a*-9*c* illustrate a similar damper mechanism 840 that allows for easy filling of the damper fluid 851 into the channel 857 of the frame member 850. The damper member 842 is then applied, whereby the angled protrusion 843 wedges in and distributes the damper fluid 851 to a single channel 860 between the first protrusion 843 and the first and second sidewalls 856, 858. In this example, a protrusion 844*a* engages a notch 858*a* formed on the second sidewall 858. Similarly, in FIG. 10, the components of the damper mechanism 940 are essentially reversed. In other words, like in FIGS. 6*a*-7, the damper member 942 is generally U-shaped defining a channel 946 between an inner sidewall 943*a* and an outer sidewall 943*b*. The damper member 942 further includes a secondary channel 947 extending from the outer sidewall 943*b*. The frame member 950 includes a base portion 952, a first protrusion 953, a second protrusion 954, and a third protrusion 956. The damper fluid 951 is inserted into the channel 946, and the first protrusion 953 is inserted into the channel 946 to define the chamber 960. In this example, the second protrusion 954 is inserted into the second channel 947.

FIGS. 11-20 illustrate alternative damper mechanisms having a three-piece design. In these examples, the fluid path may be sealed and/or prolonged to ensure fluid is contained within the chamber or to allow the fluid to be easily fillable and assembled. Additionally, these components may ensure concentricity between damping surfaces. These damping mechanisms include similar features as those described with reference to FIGS. 1-10, and thus include similar two-digit suffixes. Accordingly, for the sake of brevity, some of these components may not be described in substantial detail.

Figure 11:
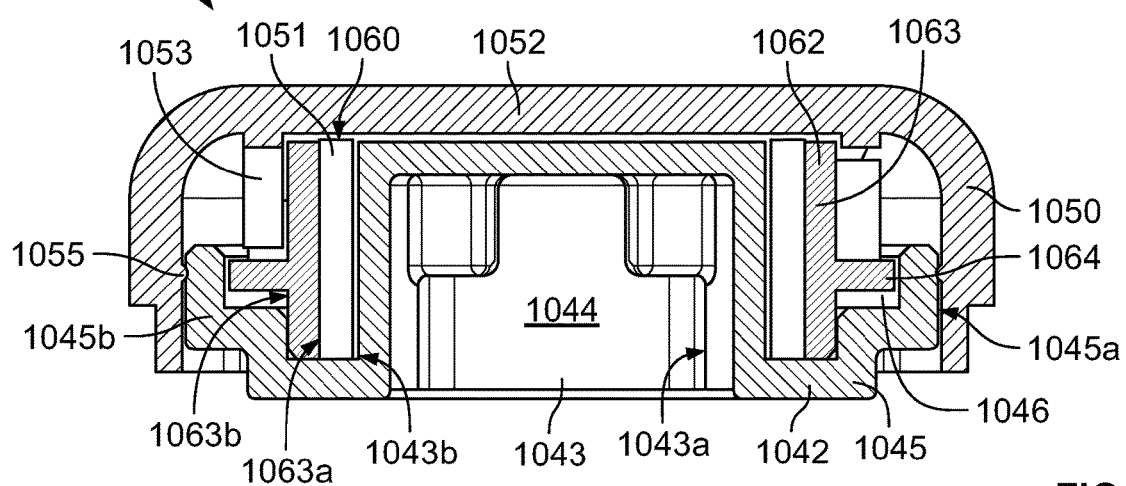
FIG. 11 illustrates a cross-sectional view of a tenth example damper mechanism of a drug delivery device in accordance with various embodiments.

As illustrated in FIG. 11, the damper mechanism 1040 includes a first damper member 1042, a frame member 1050, and a second damper member 1062. The first damper member 1042 may be coupled to the plunger rod guide (not illustrated) via any number of approaches, and includes a body 1043 having an inner surface 1043a that defines a central opening or bore 1044 to accommodate a portion of the plunger rod guide and further defines an outer surface 1043b. The first damper member 1042 also includes a winged portion 1045 having an inner surface 1045a positioned away from the body 1043 that faces the outer surface 1043b thereof. A channel 1046 is formed between the outer surface 1043b of the body 1043 and the inner surface 1045a of the winged portion 1045.

The second damper member 1062 is in the form of a generally cylindrical body 1063 having an inner surface 1063a and an outer surface 1063b. The second damper member 1062 includes a ledge 1064 extending outwardly from the outer surface 1063b. The second damper member 1062 is adapted to be at least partially disposed within the channel 1046 and at least partially surround the body 1043 of the first damper member 1042 to form concentric cylinders. When in this configuration, a chamber 1060 is formed between the outer surface 1043b of the first damper member 1042 and the inner surface 1063a of the second damper member 1062. This chamber 1060 accommodates the damper fluid 1051.

In this example, the frame member 1050 is integrally formed with the distal end 1002b of the housing 1002 and includes a base portion 1052 and a generally cylindrical protrusion 1053 extending therefrom. In operation, the frame member 1050 is placed in or near the channel 1046 and may engage the ledge 1064 of the second damper member 1062 to retain the second damper member in place. The frame member 1050 may include any number of additional notches, tabs, and the like to selectively engage the first and/or second damper members 1042, 1062. As a result, the chamber 1060 may be defined by the outer surface 1043b of the first damper member 1042, the inner surface 1063a of the second damper member 1062, and the base portion 1052 of the frame member 1050. Further, the first damper member 1042, the second damper member 1062, and the frame member 1050 form three concentric cylinders, thereby limiting relative movement (except for relative rotation) therebetween. In some examples, the second damper member 1062 may be fixedly coupled to the frame member 1050 (which itself may be coupled to and/or integrally formed with the housing 1002) to ensure that the second damper member 1062 remains fixed while the first damper member 1042 rotates with the plunger rod guide. Further, in some examples, the frame member 1050 may include a detent 1055 that engages with a groove 1045b on the winged portion 1045 of the first damper member 1042 to restrict relative axial movement.

Figure 12:
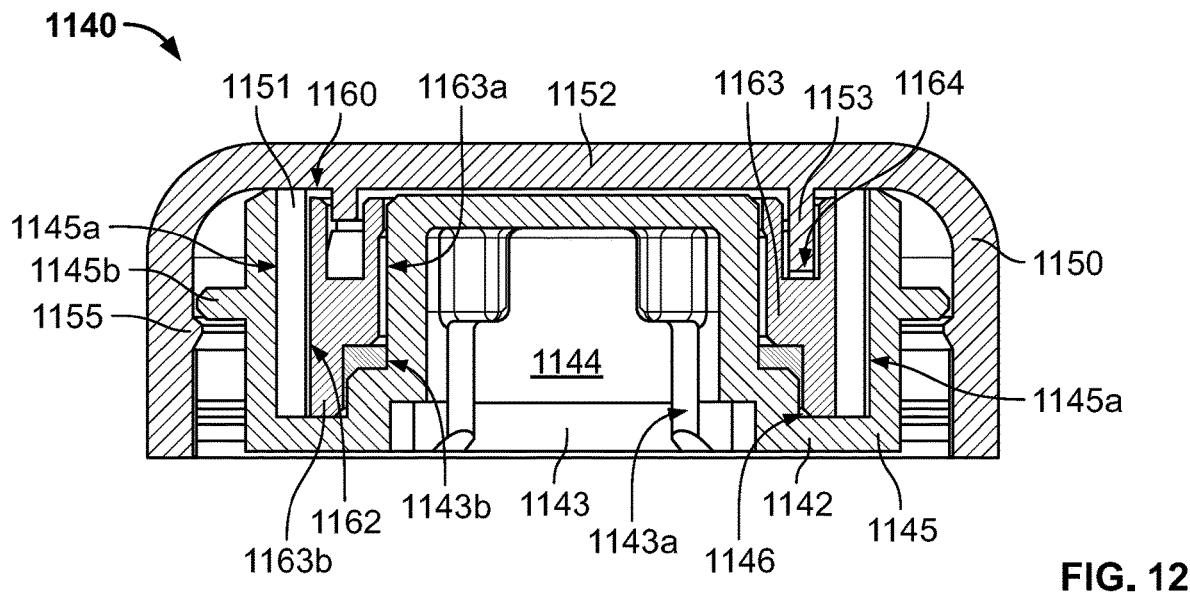
FIG. 12 illustrates a cross-sectional view of a eleventh example damper mechanism of a drug delivery device in accordance with various embodiments.

The example damper mechanism 1140 illustrated in FIG. 12 is similar to the damper mechanism 1040 (and thus, similar features include similar two-digit suffixes), but differs in the placement of the chamber 1160 and damper fluid 1151. Specifically, the chamber 1160 is defined by the inner surface 1145a of the winged portion 1145, the outer surface 1163b of the body 1163 of the second damper member 1162, and the base portion 1152 of the frame member 1150. In this example, the frame member 1150 includes a protrusion 1153 that inserts into a channel 1164 defined by the second damper member 1162 to secure the frame member 1150 to the second damper member 1162.

Figure 13:
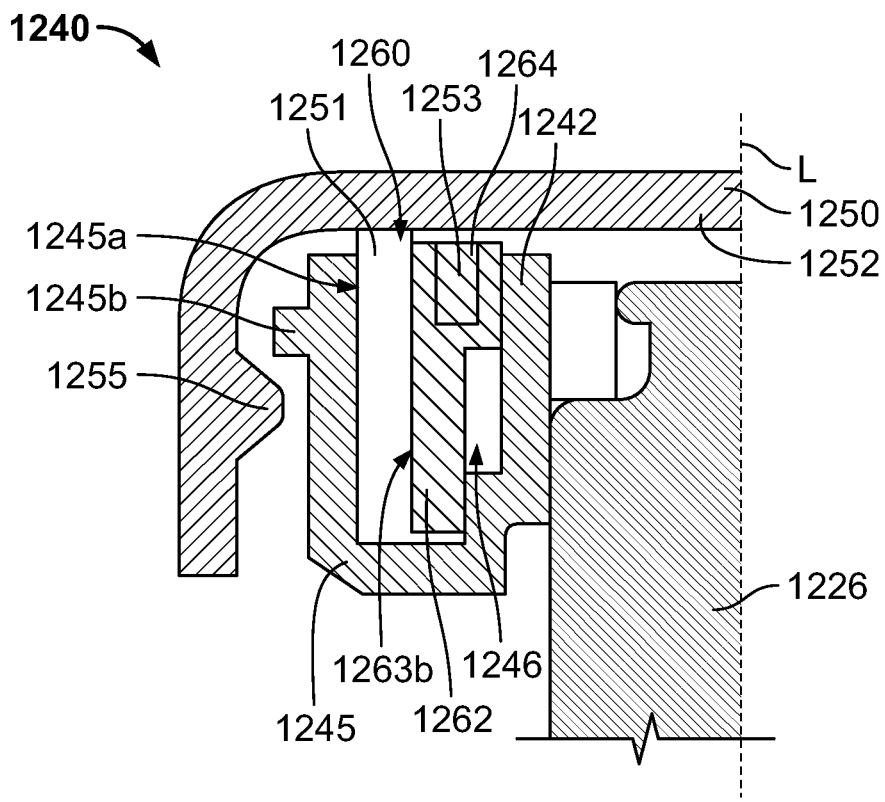
FIG. 13 illustrates a cross-sectional view of a twelfth example damper mechanism of a drug delivery device in accordance with various embodiments.

The example damper mechanism 1240 illustrated in FIG. 13 is similar to the damper mechanism 1140 (and thus, similar features include similar two-digit suffixes), but differs in that the frame member 1250 includes a rotational locking protrusion 1253 in the form of a pin that engages a cylinder or bore 1264 defined by the second damper member 1262. As such, relative rotation between the frame member 1250 and the second damper member 1262 is restricted.

Figure 14:
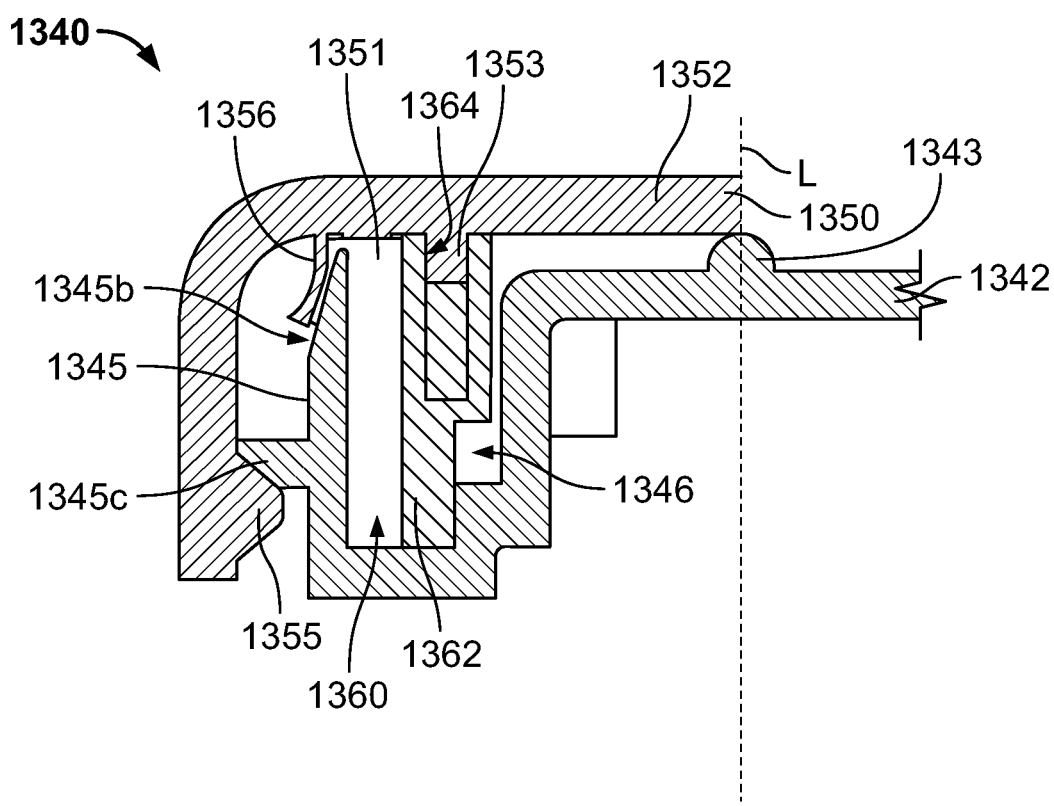
FIG. 14 illustrates a cross-sectional view of a thirteenth example damper mechanism of a drug delivery device in accordance with various embodiments.

The example damper mechanism 1340 illustrated in FIG. 14 is similar to the damper mechanism 1240 (and thus, similar features include similar two-digit suffixes), but differs in that the damper mechanism 1340 includes any number of sealing components to seal the chamber 1360 in order to retain the damper fluid 1351 therein. Specifically, the frame member 1350 additionally includes a resilient finger portion 1356 adapted to form a seal with the outer surface 1345b of the winged portion 1345 of the first damper member 1342. In this example, the winged portion 1345 has a generally tapered or wedge-like shape to assist in properly seating the resilient finger 1356 against the outer surface 1345b thereof. Additionally, the first damper member 1342 an additional seal in the form of a bump or detent 1343 to abut against the base portion 1352 of the frame member 1350.

Figure 15:
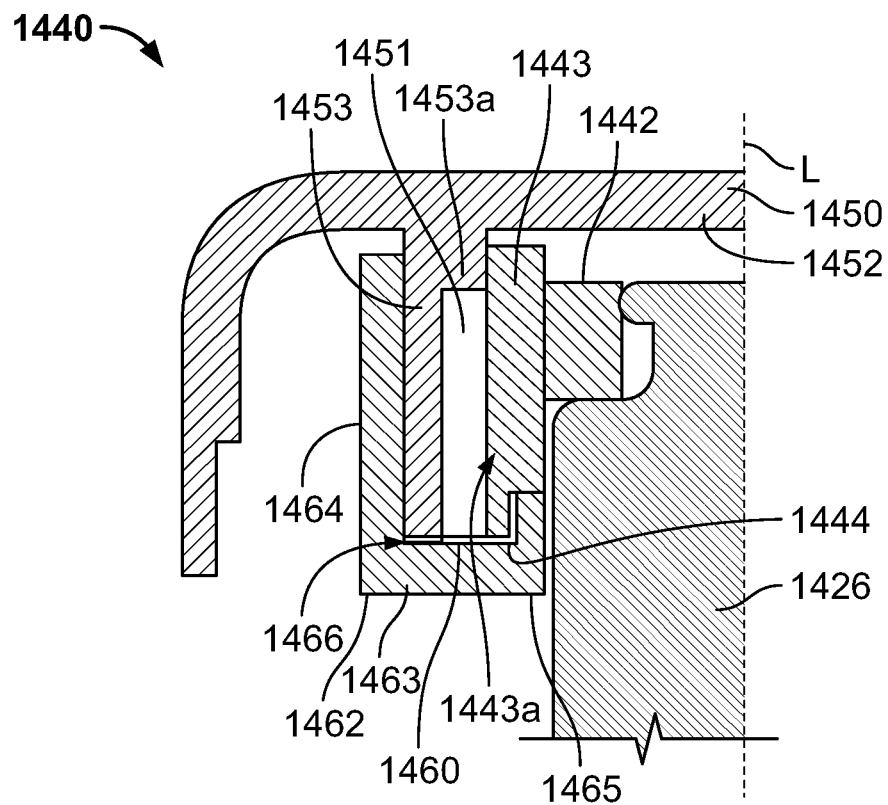
FIG. 15 illustrates a cross-sectional view of a fourteenth example damper mechanism of a drug delivery device in accordance with various embodiments.

The example damper mechanism 1440 illustrated in FIG. 15 is similar to the previously-described three piece damper mechanisms (and thus, similar features include similar two-digit suffixes), but may advantageously provide for easy filling of the chamber 1460 with damper fluid 1451 and further may include any number of seating features to ensure the components are properly aligned during installation. Specifically, a protrusion 1453 formed by the base portion 1452 of the frame member 1450 may include a ledge 1453a that assists in properly seating the first damper member 1442 against the frame member 1450. The outer surface 1443a of the first damper member 1442 abuts against the ledge 1453a to ensure that the frame member 1450 is properly concentrically arranged relative to the first damper member 1442 and to additionally define the chamber 1460 as being between the outer surface 1443a, the ledge 1453a, and the protrusion 1453. The chamber 1460 may then be filled with damper fluid 1451, and the second damper member 1462, in the form of a fitted or press-fit lid, may be applied.

The second damper member 1462 includes a base portion 1463, a first protrusion 1464, and a second protrusion 1465 that cooperate to define a channel 1466. When the second damper member 1462 is installed, the first protrusion 1464 abuts against the protrusion 1453 of the frame member 1450, and the second protrusion 1465 additionally engages a ledge 1444 of the first damper member 1442. As a result, the protrusion 1453 of the base member 1450 and the ledge 1444 of the first damper member 1442 cooperate to guide placement of the second damper member 1462 to reduce and/or eliminate relative misalignment of these components. The second damper member 1462 also acts as a seal to close off the chamber 1460.

Figure 16:
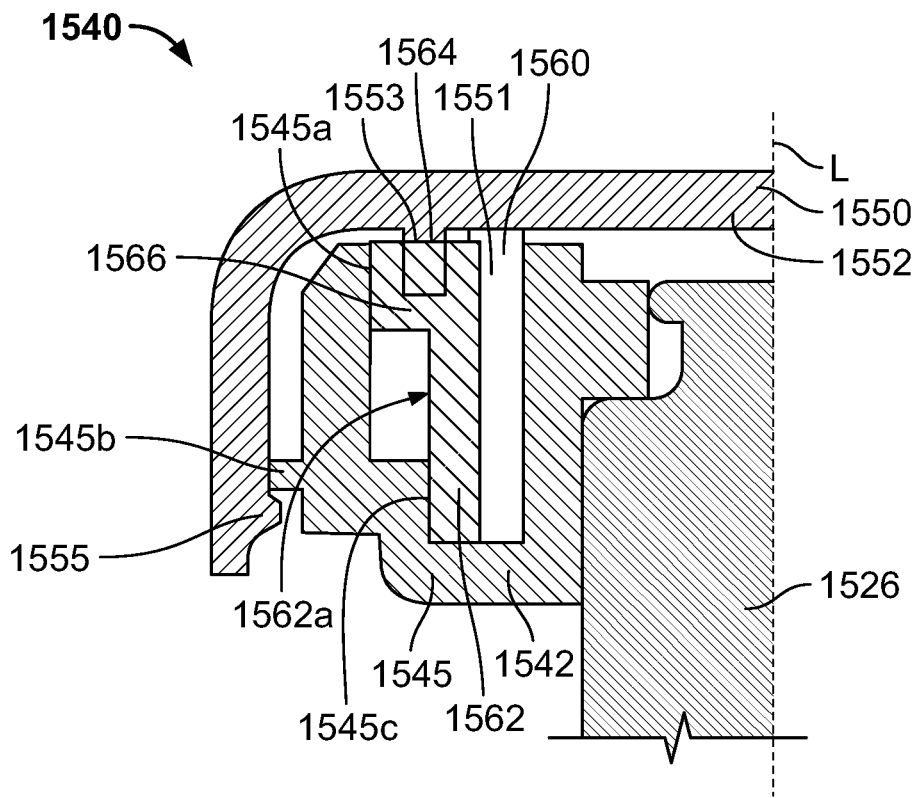
FIG. 16 illustrates a cross-sectional view of a fifteenth example damper mechanism of a drug delivery device in accordance with various embodiments.

The example damper mechanism 1540 illustrated in FIG. 16 is similar to the previously-described three piece damper mechanisms (and thus, similar features include similar two-digit suffixes), but includes an alternative seating arrangement to ensure the components are properly aligned during installation. The damper mechanism 1540 includes a first damper member 1542 having a winged portion 1545 that defines a first surface 1545*a*, a tab 1545*b*, and a second surface or ledge 1545*c*. The second damper member 1562 includes a cylinder or bore 1564 that couples to a rotational locking protrusion 1553 carried by the body portion 1552 of the frame member 1550. The second damper member 1562 additionally includes a facing surface 1562*a* and a ledge 1566. The first surface 1545 of the winged portion 1545 is adapted to abut the ledge 1566 of the second damper member 1562, and the second surface 1545*c* of the winged portion 1545 is adapted to abut the facing surface 1562*a* of the second damper member 1562, thereby creating two points of contact or seating surfaces. Accordingly, proper displacement of the damper mechanism 1540 is further ensured.

Figure 17:
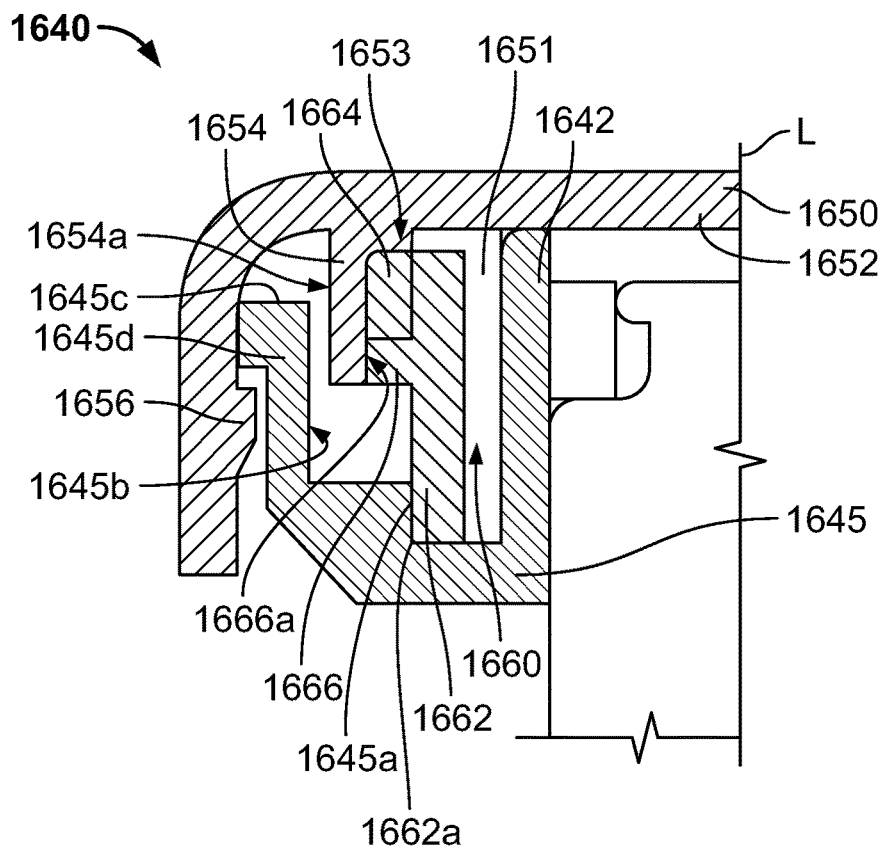
FIG. 17 illustrates a cross-sectional view of a sixteenth example damper mechanism of a drug delivery device in accordance with various embodiments.
Figure 18:
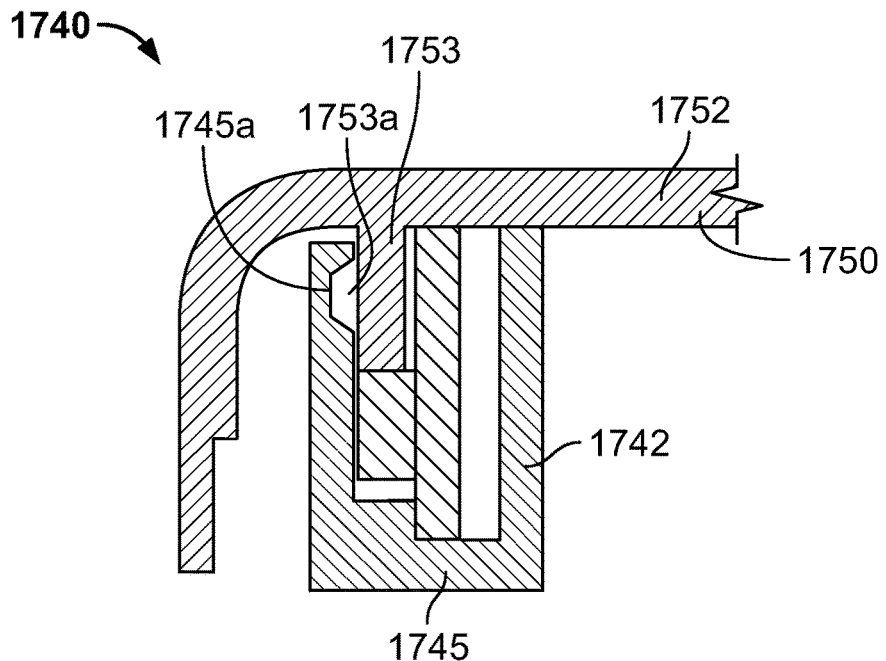
FIG. 18 illustrates a cross-sectional view of a seventeenth example damper mechanism of a drug delivery device in accordance with various embodiments.

FIGS. 17 and 18 illustrate damper mechanisms 1640, 1740 that are similar to the damper mechanisms 1240, 1340, 1440, and 1540 (and thus, similar features include similar two-digit suffixes), but differ in that they use features of their respective frame members 1650, 1750 as a seating surface. Specifically, in FIG. 17, the first damper member 1642 includes a finger portion 1645 having a first ledge or surface 1645*a*, a second surface 1645*b*, a finger 1645*c*, and a protrusion 1645*d* extending from the finger 1645*c*. The frame member 1650 includes a base portion 1652 carrying a first protrusion 1653 which locks relative rotation, and a second protrusion 1654 having an outer surface 1654*a*. The frame member 1650 further includes a tab 1656. The second damper member 1662 includes a first surface 1662*a*, a channel or hole 1664, and a ledge 1666 defining a surface 1666*a*. The first protrusion 1653 of the frame member 1650 is inserted into the hole 1664 of the second damper member 1662 to prevent relative rotation therebetween. Additionally, the surface 1666*a* of the ledge 1666 of the second damper member 1662 abuts against the second protrusion 1654 of the frame member 1652. The first surface 1662*a* of the second damper member 1662 abuts against the first ledge 1645*a* of the finger portion 1645 of the first damper member 1642, and the second surface 1645*b* of the finger portion 1645 of the first damper member 1642 abuts against the outer surface 1654*a* of the second protrusion 1654 of the frame member 1650. Additionally, the finger 1645*c* of the finger portion 1645 engages the tab 1656 of the frame member 1656. Accordingly, multiple points of contact or seating surfaces are created between the first damper member 1642, the frame member 1650, and the second damper member 1662 to further ensure proper displacement of the damper mechanism 1640. In FIG. 18, the damper mechanism 1740 includes similar features, surfaces, and/or ledges as the damper mechanism 1640 illustrated in FIG. 17, but the frame member 1750 additionally includes a protrusion 1753 that carries a bump 1753*a* that engages a channel 1745*a* of the finger portion 1745 of the first damper member 1742.

Figure 19:
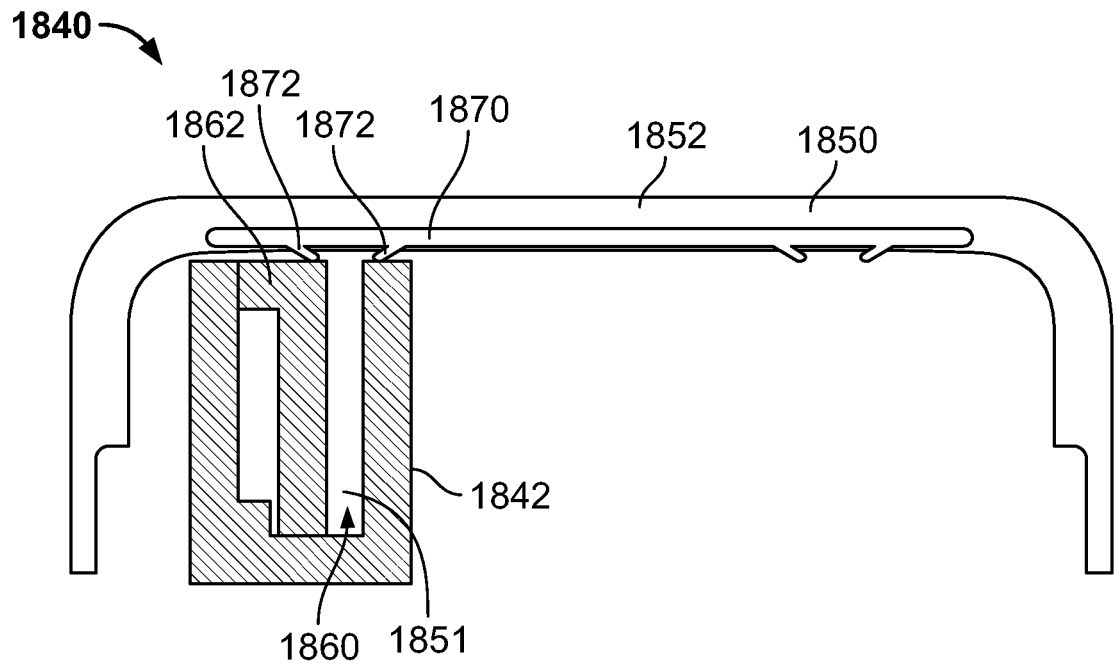
FIG. 19 illustrates a cross-sectional view of a eighteenth example damper mechanism of a drug delivery device in accordance with various embodiments.
Figure 20:
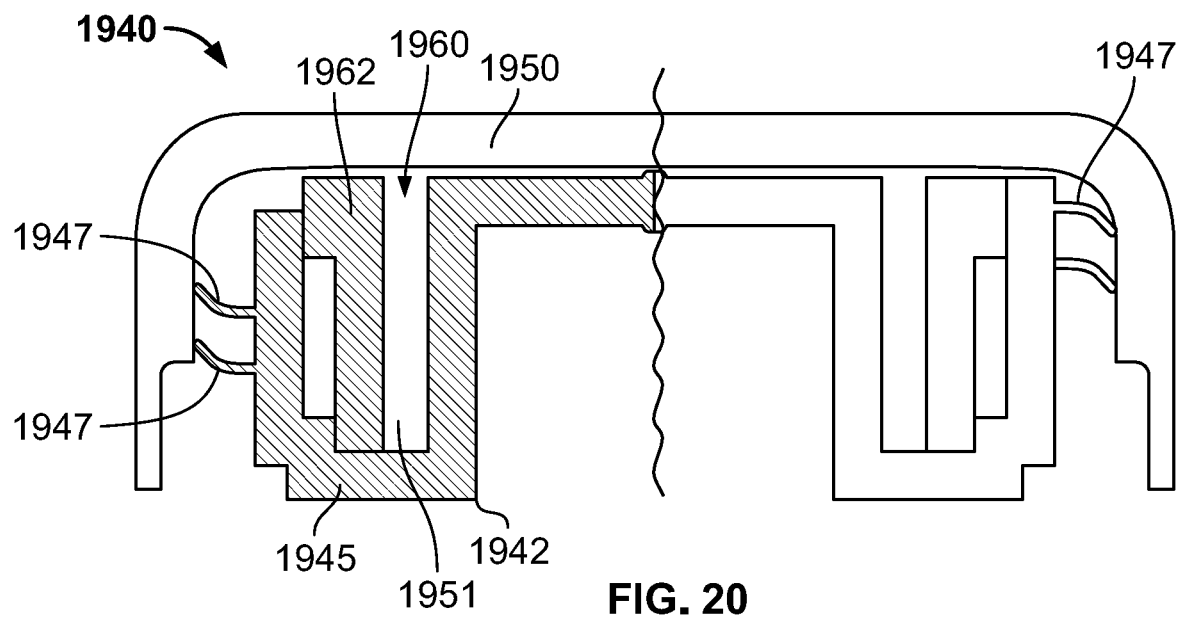
FIG. 20 illustrates a cross-sectional view of a nineteenth example damper mechanism of a drug delivery device in accordance with various embodiments.

The example damper mechanisms illustrated in FIGS. 19 and 20 are similar to the previously-described damper mechanisms (and thus, similar features include similar two-digit suffixes), but include an additional sealing components. As illustrated in FIG. 19, a sealing member 1870 is operably coupled (e.g., glued or otherwise affixed) to the frame member 1850. The sealing member 1870 can be molded using any number of conventional approaches, and includes a number of resilient sealing fingers 1872. These fingers 1872 are at least partially inserted into the chamber 1860 to restrict the damper fluid 1851 from exiting the chamber 1860 in the event that a gap is formed between the frame member 1850 and the first damper member 1842 and/or the second damper member 1862.

In FIG. 20, the resilient sealing fingers 1947 are carried by the finger portion 1945 of the first damper member 1945. These sealing fingers 1947 engage the frame member 1950 to ensure that damper fluid 1951 does not leak into the remainder of the device 1900.

Figure 24:
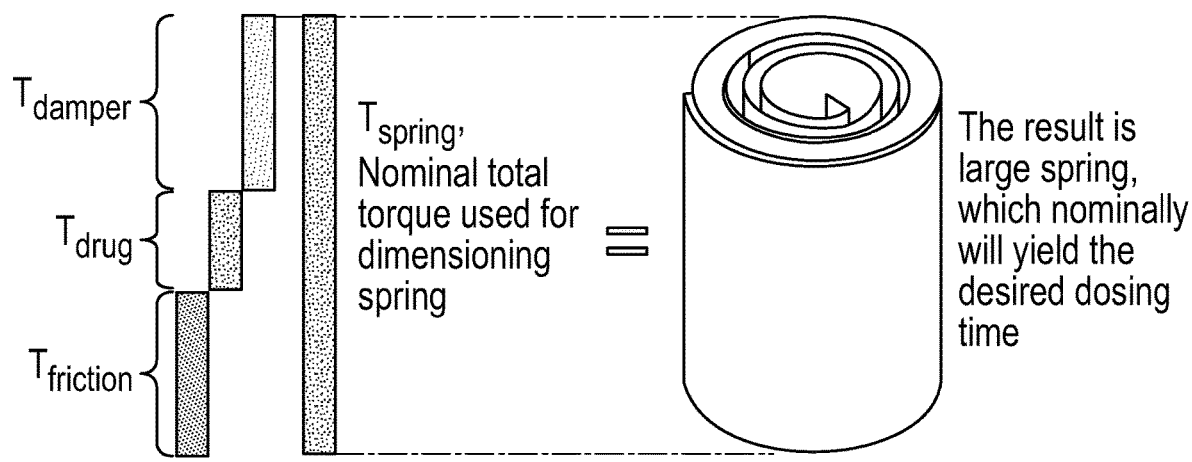
FIG. 24 illustrates an illustration of an example of the effect of a damper mechanism on drug expulsion in accordance with various embodiments.
Figure 25:
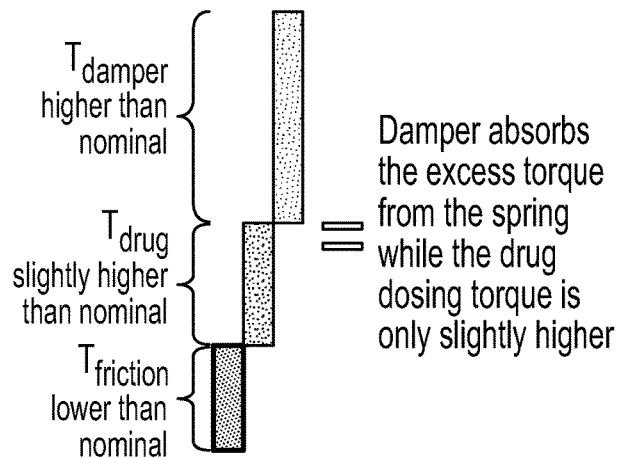
FIG. 25 illustrates an illustration of an example of the effect of a damper mechanism on drug expulsion in a low-friction environment in accordance with various embodiments.
Figure 26:
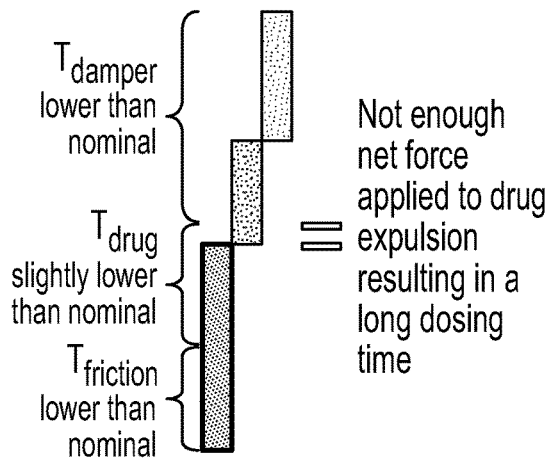
FIG. 26 illustrates an illustration of an example of the effect of a damper mechanism on drug expulsion in a high-friction environment in accordance with various embodiments.

Turning to FIGS. 24-26, in some examples, it may be advantageous to construct the syringe barrel 112 out of different materials. Because of high friction variation in containers constructed from some materials, there may be significant variance in delivery times. The friction between the plunger and the syringe barrel may result in substantial variation, especially when the syringe is constructed from a polymeric material. As noted, the force required for expelling the drug through the needle in a specified time, which is directly linked to the axial plunger velocity, varies with the viscosity of the drug. For high-viscosity drugs (e.g., above 10-15 cP), the force requirement is high, and for low viscosity drugs, the force requirement is low. The force is also dependent on the velocity at which the drug is expelled. During dosing, an equilibrium dosing velocity is achieved where the velocity-dependent resistance in the system matches the input torque from the power source. However, the range in which the frictional forces vary in the system is constant regardless of the viscosity of the drug. Consequently, the ratio between frictional forces and drug expulsion force becomes high in the case of low-viscosity drugs. Further, since a high variability in the frictional forces is expected for polymer syringe barrels, the remaining torque from the spring for expelling the drug can either be too high or too low, resulting in too fast or too slow dosing time. This can result in either unacceptably high variations in dosing times or that the device stalls altogether.

The use of a damper mechanism addresses these inconsistencies by acting as a buffer of excess torque. The velocity of the dosing mechanism is the result of a mechanical equilibrium, in which the friction in the system, the torque required to expel the drug, and the torque acting on the mechanical damper is equal to the total input torque from the power source. Because the non-constant torques, the damper torque and the torque required the expel the drug added, become more dominant than the frictional forces, the variation in the frictional forces will have less relative impact on the available torque for the expulsion, and will therefore affect the velocity modestly. Generally, whenever the resistance in the device increases—be it during dosing due to friction and component tolerances, or because of a higher drug viscosity—the velocity in the device decreases. However, because of the velocity-dependence of the damper, an infinitesimal decrease in velocity leads to a lower damping torque, which in turn frees up available torque for overcoming the increased resistance.

As shown in FIGS. 24-26, the variances between plunger friction, torque required to expel the drug, and torque absorbed by the damper are added to provide a nominal input torque requirement. It is noted that the torque contributions in the device are not limited to these provided terms. Because the damper dissipates a substantial amount of torque, the spring is dimensioned larger than if no damper was used. The velocity-dependent terms (i.e., $T_{damper}$ and $T_{drug}$) dissipate the majority of the energy in the device.

Because a small decrease in velocity corresponds to a large decrease in damper torque (and vice-versa), only a minor change in available torque for drug expulsion is observed. This is illustrated in FIGS. 25 and 26: in case 1, shown in FIG. 25, the friction is in the lower end of the expected range, which results in the viscous terms to increase in magnitude because of more available torque, where the damper term will absorb the most torque while the torque available for drug expulsion increases only slightly. This results in only a slightly faster dosing time. Conversely, in case 2 illustrated in FIG. 26, an increase friction results in the damper torque decreasing substantially, while the available torque for drug expulsion decreases only slightly, thus yielding only a slightly longer dosing time. In devices without damper mechanisms, a substantial percentage of the input torque is used for overcoming the friction in the system. In variation in friction will directly add or subtract substantially on the available torque for the expulsion part. High fluctuations can therefore be expected at dosing time.

Figure 27:
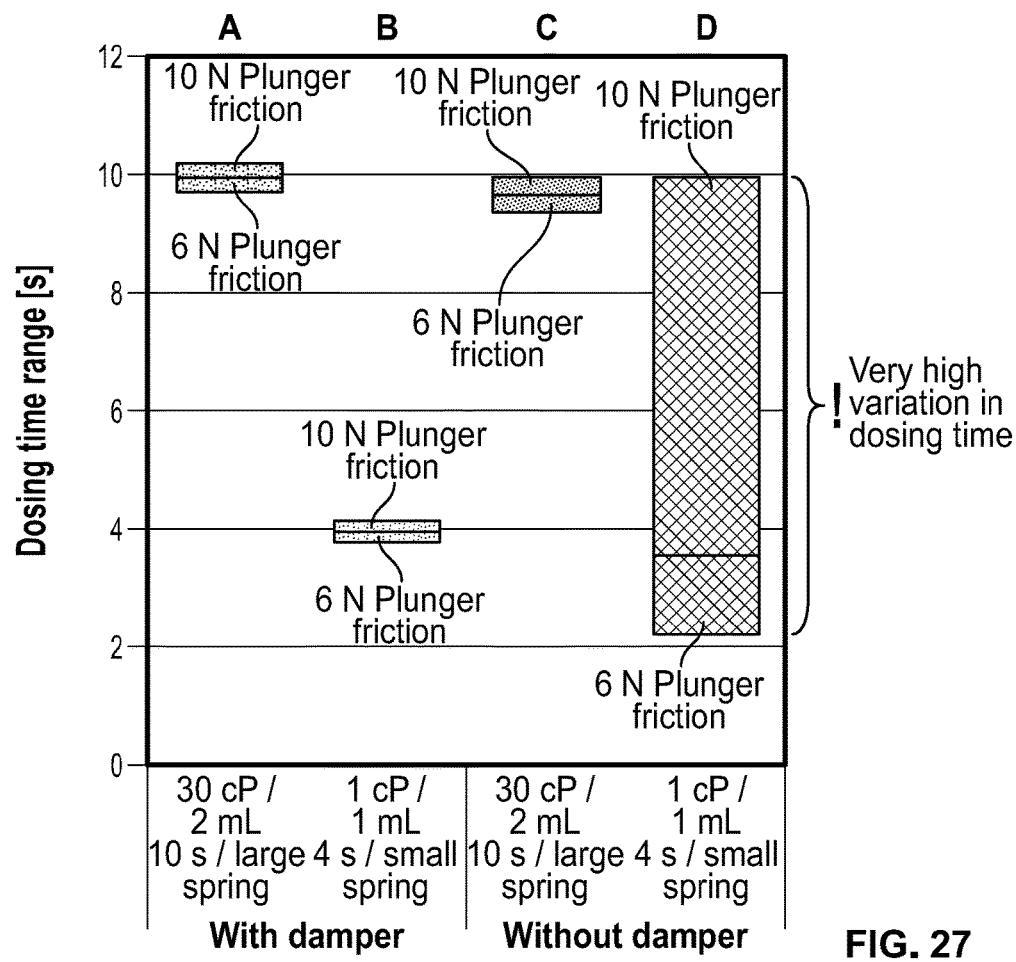
FIG. 27 illustrates example model calculations for a drug delivery device in accordance with various embodiments.

Turning to FIG. 27, an example of the high sensitivity is illustrated by model calculations. The first two columns A and B illustrate the range of dosing times for a range of friction values where a mechanical damper mechanism is used. Both the high viscosity (column A) and low viscosity (column B) drug variant devices exhibit a narrow variation in dosing time thanks to the damper. For the variants without a damper (columns C and D), the variability is similarly low for high viscosity drug variants. This is attributed to the high proportion of the input torque spent on expelling the drug relative to the torque used for overcoming the constant friction. However, for the low viscosity drug variant (column D), where no damper is used, the dosing time varies dramatically with the friction variance. In addition to the high dosing time sensitivity towards friction variability, in terms of a device platform, any change in drug viscosity will substantially change the input torque requirements if no damper is used. Therefore, in order to achieve the desired window of doing times, a higher number of power springs would be required. Having a damper, on the other, introduces the buffering phenomenon at the expense of a slightly larger spring.

Additionally, certain materials may impact these forces. For example, when using a glass syringe, due to the siloconization of the barrel and the stopper, there may be a lower glide force, and lower variation of the glide force relative to plastic syringes. When administering drugs having high viscosities, the resistance of flow through the needle tends to be the largest contributor to overall injection times. However, when administering drugs having low viscosities and volumes, the glide force (and its relative variability) can be a large contributor to the total required force in the system.

So configured, the above damper designs can reduce the number of required spring variants in an autoinjector platform, can improve consistency of dose times for users, and can reduce risks of syringe breakages. Because minor variations in spring performance and/or drug viscosity can have a significant impact when using low-viscosity drugs, the damper mechanisms described herein slows all dose times, thereby requiring fewer spring variants. When using drugs having high viscosities, the damper mechanisms described herein have a greater effect on the impact speed of the plunger rod, especially when administering low volume drug products. The damper mechanism will reduce the impact speed of the plunger rod to a safer level to reduce the risk of damaging the syringe. The damper mechanisms described herein require fewer parts, thereby assisting in assembly and cost reduction. Additionally, the damper mechanisms described do not rely on surface friction and relatively complex moving mechanisms and thus further reduce system complexities.

The above description describes various assemblies, devices, and methods for use with a drug delivery device. It should be clear that the assemblies, drug delivery devices, or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749;

2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of sequence identification number:2 as set forth therein in FIG. 2 and/or the heavy chain of sequence identification number:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of sequence identification numbers: 305-351, including TN8-19-1 through TN8-19-40, TN8-19 con1 and TN8-19 con2; peptibodies of the mL2 family of sequence identification numbers:357-383; the mL15 family of sequence identification numbers:384-409; the mL17 family of sequence identification numbers:410-438; the mL20 family of sequence identification numbers:439-446; the mL21 family of sequence identification numbers:447-452; the mL24 family of sequence identification numbers:453-454; and those of sequence identification numbers:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4(N), Con4(N) 1K WT, 2xCon4(N) 1K; L1C; L1C 1K; 2xL1C; Con4C; Con4C 1K; 2xCon4C 1K; Con4-L1 (N); Con4-L1C; TN-12-9(N); C17 (N); TN8-8(N); TN8-14(N); Con 1(N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AblP; and AblP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v 1.0, huEM164 v 1.1, huEM164 v 1.2, and huEM164 v 1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication No. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF$_{(K)}$, deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences sequence identification number:1 and sequence identification number:7 respectively therein); 5D (having light chain variable and heavy chain variable sequences sequence identification number:2 and sequence identification number:9 respectively therein); 2H (having light chain variable and heavy chain variable sequences sequence identification number:3 and sequence identification number:10 respectively therein); 43H (having light chain variable and heavy chain variable sequences sequence identification number:6 and sequence identification number:14 respectively therein); 41H (having light chain variable and heavy chain variable sequences sequence identification number:5 and sequence identification number:13 respectively therein); and 15H (having light chain variable and heavy chain variable sequences sequence identification number:4 and sequence identification number:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of sequence identification number:17 and the light chain of sequence identification number:18; those having the heavy chain variable region of sequence identification number:6 and the light chain variable region of sequence identification number:8; those having the heavy chain of sequence identification number:19 and the light chain of sequence identification number:20; those having the heavy chain variable region of sequence identification number:10 and the light chain variable region of sequence identification number:12; those having the heavy chain of sequence identification number:32 and the light chain of sequence identification number:20; those having the heavy chain variable region of sequence identification number:30 and the light chain variable region of sequence identification number:12; those having the heavy chain sequence of sequence identification number:21 and the light chain sequence of sequence identification number:22; those having the heavy chain variable region of sequence identification number:14 and the light chain variable region of sequence identification number:16; those having the heavy chain of sequence identification number:21 and the light chain of sequence identification number:33; and those having the heavy chain variable region of sequence identification number:14 and the light chain variable region of sequence identification number:31, as disclosed in the foregoing publication. A specific antibody contemplated is antibody 1119 as disclosed in the foregoing U.S. publication and having a complete heavy chain of sequence identification number:17 as disclosed therein and having a complete light chain of sequence identification number:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising sequence identification number:8 and a light chain variable region having sequence identification number:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgrastim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Rα mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1 mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, bispecific T cell engager (BiTE®) antibodies, e.g. BLINCYTO® (blinatumomab), can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the drug delivery devices, methods, and components thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention. For example, components described herein with reference to certain kinds of drug delivery devices, such as on-body injector drug delivery devices or other kinds of drug delivery devices, can also be utilized in other kinds of drug delivery devices, such as autoinjector drug delivery devices.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. A drug delivery device comprising:
   a housing defining a shell having a proximal end, a distal end, and a longitudinal axis extending between the proximal end and the distal end thereof;
   a needle assembly at least partially disposed within the housing at the proximal end thereof, the needle assembly comprising a syringe barrel containing a medicament and a needle or a cannula;
   a drive assembly at least partially disposed within the housing and operably coupled to the needle assembly to urge the medicament through the needle or cannula; and
   a damper mechanism at least partially disposed within the housing, the damper mechanism being operably coupled to the drive assembly, wherein, upon activating the drive assembly, the damper mechanism exerts a torque on at least one component operably coupled to the drive assembly to dampen an effect of the drive assembly.

2. The drug delivery device of claim 1, wherein the damper mechanism comprises:
   a frame member;
   a damper member operably coupled to the drive assembly;
   a chamber formed between a portion of the frame member and the damper member; and
   a damper fluid disposed within the chamber formed between the frame member and the damper member.

3. The drug delivery device of claim 2, wherein the frame member is integrally formed with the housing.

4. The drug delivery device of claim 2, further comprising an excess chamber fluidly coupled to the chamber, the excess chamber adapted to receive excess damper fluid.

5. The drug delivery device of claim 2, further comprising a seal disposed near the chamber to retain the damper fluid within the chamber.

6. The drug delivery device of claim 2, wherein the chamber is one of (a) through (c):
   (a) axially aligned with the longitudinal axis,
   (b) partially axially aligned and partially transversely aligned with the longitudinal axis, or
   (c) transversely aligned with the longitudinal axis.

7. The drug delivery device of claim 2, wherein the drive assembly comprises:
   a plunger assembly comprising a threaded plunger rod and a plunger face being disposed near the needle assembly and being moveable along the longitudinal axis of the housing;
   a plunger rod guide coupled to the plunger assembly to guide rotational movement of the plunger assembly, the plunger rod guide further being operably coupled to one of the frame member or the damper member; and
   a torque spring coupled to the plunger rod guide to exert a force on the plunger rod guide that causes the plunger rod guide to rotate, wherein rotation of the plunger rod guide causes the plunger assembly to advance towards the proximal end of the housing to urge the medicament through the needle assembly.

8. The drug delivery device of claim 7, wherein the plunger assembly includes a clearance of greater than 10 mm between the threaded plunger rod and the plunger face, wherein the syringe barrel is adapted to contain at least approximately 1 mL of medicament having a viscosity of at least approximately 4 cP.

9. The drug delivery device of claim 1, wherein the damper mechanism exerts the torque on the drive assembly.

10. A damper mechanism for a drug delivery device comprising:
    a frame member;
    a damper member operably coupled to a drive assembly of the drug delivery device;
    a chamber formed between a portion of the frame member and the damper member; and
    a damper fluid disposed within the chamber formed between the frame member and the damper member;
    wherein upon activating the drug delivery device to administer a medicament to a user, the frame member and the damper member rotate relative to each other and the damper fluid exerts an opposing force on at least one of the frame member and the damper member.

11. The damper mechanism of claim 10, wherein the frame member is formed integrally with a housing of the drug delivery device.

12. The damper mechanism of claim 10, wherein the damper member defines a channel, and the frame member defines protrusion extending inwardly into channel.

13. The damper mechanism of claim 10, wherein the frame member defines an elongated platform having an opening and the damper member defines a disk having a protrusion disposed through the platform opening, wherein the chamber is formed by the volume between the elongated platform and the disk.

14. The damper mechanism of claim 10, further comprising an excess chamber fluidly coupled to the chamber, the excess chamber adapted to receive excess damper fluid.

15. The damper mechanism of claim 10, further comprising a seal disposed near the chamber to retain the damper fluid within the chamber.

16. The damper mechanism of claim 10 wherein the chamber is one of (a) through (c):
 (a) axially aligned with the longitudinal axis,
 (b) partially axially aligned and partially transversely aligned with the longitudinal axis, or
 (c) transversely aligned with the longitudinal axis.

17. The damper mechanism of claim 10, wherein the damper assembly is adapted to engage at least one of a housing of a drug delivery device or a drive assembly of the drug delivery device.

18. The damper mechanism of claim 17, wherein the damper mechanism is adapted to be assembled to the drug delivery device via an axial assembly.

19. The drug delivery device of claim 1, wherein the at least one component includes a plunger rod guide.

20. The drug delivery device of claim 2, wherein, upon activating the drive assembly of the drug delivery device, the frame member and the damper member rotate relative to each other, and the damper fluid exerts an opposing force on at least one of the frame member and the damper member.

21. The drug delivery device of claim 2, wherein, upon activating the drive assembly of the drug delivery device, the damper member rotates relative to the frame member, and the damper fluid exerts an opposing force on at least one of the frame member and the damper member.

22. The drug delivery device of claim 2, wherein the torque exerted by the damper mechanism on the at least one component operably coupled to the drive assembly is related to an amount of shear stress in the damper fluid.

23. The drug delivery device of claim 1, wherein the damper mechanism is at least partially disposed within the housing adjacent to the distal end thereof.

\* \* \* \* \*